US012426864B2

(12) United States Patent
Stephenson et al.

(10) Patent No.: US 12,426,864 B2
(45) Date of Patent: Sep. 30, 2025

(54) HEMOSTASIS DEVICES AND METHODS OF USE (71) Applicant: Merit Medical Systems, Inc., South Jordan, UT (US)

(72) Inventors: Richard Stephenson, Salt Lake City, UT (US); Aaron Hopkinson, Herriman, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 376 days.

(21) Appl. No.: 17/806,653

(22) Filed: Jun. 13, 2022

(65) Prior Publication Data

US 2022/0401086 A1    Dec. 22, 2022

Related U.S. Application Data (60) Provisional application No. 63/212,227, filed on Jun. 18, 2021.

(51) Int. Cl.
*A61B 17/00* (2006.01)
*A61B 17/12* (2006.01)
*A61B 17/135* (2006.01)

(52) U.S. Cl.
CPC ........ *A61B 17/0057* (2013.01); *A61B 17/135* (2013.01); *A61B 2017/00659* (2013.01); *A61B 2017/12004* (2013.01)

(58) Field of Classification Search
CPC .............. A61B 17/0057; A61B 17/135; A61B 2017/00659; A61B 2017/12004; A61B 17/1322; A61B 2017/00907
See application file for complete search history.

(56) References Cited

U.S. PATENT DOCUMENTS

| 2,547 A | 4/1842 | Welchman |
| 44,843 A | 10/1864 | Smith |
| 1,177,208 A | 3/1916 | Pierpont |
| 1,197,232 A | 9/1916 | Pierpont |

(Continued)

FOREIGN PATENT DOCUMENTS

| CA | 2546434 | 1/2013 |
| CN | 201205292 | 3/2009 |

(Continued)

OTHER PUBLICATIONS

Office Action dated Jul. 25, 2017 for U.S. Appl. No. 15/081,783.

(Continued)

*Primary Examiner* — Andrew P. Restaino
(74) *Attorney, Agent, or Firm* — Dorsey & Whitney LLP (57) ABSTRACT

A hemostasis device configured to apply a compressive force to a puncture site of a patient's vessel, such as an artery of the foot, is disclosed. The hemostasis device may include a compression member having a plurality of tabs and an inflatable bladder. A plurality of bands may be used to position and maintain the compression member over the puncture site until hemostasis is achieved are releasably coupled to the plurality of tabs. A first band can wrap around the ankle, a second band can wrap around the foot, and a third band can extend between two toes or around a toe. The hemostasis device may also comprise an inflation port in fluid communication with the inflatable bladder.

18 Claims, 7 Drawing Sheets

(56) References Cited

U.S. PATENT DOCUMENTS

| | | |
|---|---|---|
| 1,281,653 A | 10/1918 | Plummer |
| 2,332,107 A | 10/1943 | Nieburgs |
| 3,003,500 A | 10/1961 | Barton et al. |
| 3,021,841 A | 2/1962 | Burke |
| 3,050,064 A | 8/1962 | Moore et al. |
| 3,115,138 A | 12/1963 | Mcelvenny et al. |
| 3,233,610 A | 2/1966 | Wade |
| 3,241,554 A | 3/1966 | Coanda |
| 3,253,594 A | 5/1966 | Matthews |
| 3,312,221 A | 4/1967 | Overment |
| 3,363,626 A | 1/1968 | Bidwell et al. |
| 3,376,868 A | 4/1968 | Mondiadis |
| 3,417,750 A | 12/1968 | Carson |
| 3,419,010 A | 12/1968 | Williamson |
| 3,459,189 A | 8/1969 | Alley |
| 3,487,837 A | 1/1970 | Petersen |
| 3,542,026 A | 11/1970 | Bledsoe |
| 3,554,580 A | 1/1971 | Goyke |
| 3,566,875 A | 3/1971 | Stoehr |
| 3,572,340 A | 3/1971 | Lloyd et al. |
| 3,650,507 A | 3/1972 | Nyberg et al. |
| 3,680,562 A | 8/1972 | Wittes et al. |
| 3,683,929 A | 8/1972 | Holter |
| 3,742,952 A | 7/1973 | Magers et al. |
| 3,752,158 A | 8/1973 | Kariher |
| 3,768,476 A | 10/1973 | Raitto |
| 3,774,611 A | 12/1973 | Tussey et al. |
| 3,777,757 A | 12/1973 | Gray et al. |
| 3,783,870 A | 1/1974 | Schachet |
| 3,809,087 A | 5/1974 | Lewis |
| 3,820,546 A | 6/1974 | Chittenden et al. |
| 3,853,127 A | 12/1974 | Spademan |
| 3,875,941 A | 4/1975 | Adair |
| 3,920,023 A | 11/1975 | Dye et al. |
| 3,960,153 A | 6/1976 | Carey et al. |
| 3,982,546 A | 9/1976 | Friend |
| 4,022,209 A | 5/1977 | Nehring |
| 4,029,095 A | 6/1977 | Pena |
| 4,073,294 A | 2/1978 | Stanley et al. |
| 4,105,031 A | 8/1978 | Kurtz et al. |
| 4,112,949 A | 9/1978 | Rosenthal et al. |
| 4,116,366 A | 9/1978 | Takenakashima et al. |
| 4,120,715 A | 10/1978 | Ockwell et al. |
| 4,143,853 A | 3/1979 | Abramson |
| 4,136,696 A | 5/1979 | Nehring |
| 4,153,058 A | 5/1979 | Nehme |
| 4,170,300 A | 10/1979 | Pick |
| 4,174,053 A | 11/1979 | Shimizu |
| 4,187,848 A | 2/1980 | Taylor |
| 4,203,445 A | 5/1980 | Jessup et al. |
| 4,214,593 A | 7/1980 | Imbruce et al. |
| 4,257,629 A | 3/1981 | Maple et al. |
| 4,265,848 A | 5/1981 | Rusch et al. |
| 4,266,545 A | 5/1981 | Moss |
| 4,310,104 A | 1/1982 | Takatsuki |
| 4,315,513 A | 2/1982 | Nawash et al. |
| 4,334,551 A | 6/1982 | Pfister |
| 4,341,212 A | 7/1982 | Medwid |
| D267,433 S | 12/1982 | Pageau |
| 4,364,395 A | 12/1982 | Redmond et al. |
| D267,815 S | 2/1983 | Elliott et al. |
| 4,382,442 A | 5/1983 | Jones |
| 4,390,519 A | 6/1983 | Sawyer |
| 4,392,858 A | 7/1983 | George et al. |
| 4,393,873 A | 7/1983 | Nawash et al. |
| 4,402,682 A | 9/1983 | Garver, Sr. et al. |
| 4,421,146 A | 12/1983 | Bond et al. |
| 4,427,425 A | 1/1984 | Briggs et al. |
| 4,429,693 A | 2/1984 | Blake et al. |
| 4,433,973 A | 2/1984 | Kurtz et al. |
| 4,439,190 A | 3/1984 | Protzmann et al. |
| 4,447,235 A | 5/1984 | Clarke |
| 4,455,141 A | 6/1984 | Todd |
| 4,464,168 A | 8/1984 | Redmond et al. |
| 4,475,904 A | 10/1984 | Wang |
| 4,476,866 A | 10/1984 | Chin |
| 4,479,495 A | 10/1984 | Isaacson |
| 4,490,003 A | 12/1984 | Robinson |
| 4,501,363 A | 2/1985 | Isbey, Jr. |
| 4,511,163 A | 4/1985 | Harris et al. |
| 4,512,771 A | 4/1985 | Norton |
| 4,525,167 A | 6/1985 | Goldberg et al. |
| 4,543,100 A | 9/1985 | Brodsky |
| 4,557,262 A | 12/1985 | Snow |
| 4,564,222 A | 1/1986 | Loker et al. |
| 4,569,674 A | 2/1986 | Phillips et al. |
| 4,583,972 A | 4/1986 | Hunter, III et al. |
| 4,605,400 A | 8/1986 | Kurtz et al. |
| 4,610,469 A | 9/1986 | Wolff-Mooij |
| 4,610,671 A | 9/1986 | Luther |
| 4,620,846 A | 11/1986 | Goldberg et al. |
| 4,642,088 A | 2/1987 | Gunter |
| 4,643,720 A | 2/1987 | Lanciano |
| 4,648,870 A | 3/1987 | Goldberg et al. |
| 4,669,463 A | 6/1987 | Mcconnell |
| 4,673,398 A | 6/1987 | Turner et al. |
| 4,675,020 A | 6/1987 | Mcphee |
| 4,681,571 A | 7/1987 | Nehring |
| 4,685,908 A | 8/1987 | Kurtz |
| 4,702,733 A | 10/1987 | Wright et al. |
| 4,706,830 A | 11/1987 | Wareing |
| 4,738,671 A | 4/1988 | Elliott et al. |
| 4,740,202 A | 4/1988 | Stacey et al. |
| 4,741,678 A | 5/1988 | Nehring |
| 4,747,843 A | 5/1988 | Felix et al. |
| 4,747,844 A | 5/1988 | Elliott |
| 4,752,292 A | 6/1988 | Lopez et al. |
| 4,758,238 A | 7/1988 | Sundblom et al. |
| 4,781,674 A | 11/1988 | Redmond et al. |
| 4,790,567 A | 12/1988 | Kawano et al. |
| 4,809,679 A | 3/1989 | Shimonaka et al. |
| 4,813,929 A | 3/1989 | Semrad |
| 4,820,288 A | 4/1989 | Isono |
| 4,828,546 A | 5/1989 | Mcneil et al. |
| 4,834,702 A | 5/1989 | Rocco |
| 4,834,802 A | 5/1989 | Prier |
| 4,844,087 A | 7/1989 | Garg |
| 4,850,955 A | 7/1989 | Newkirk |
| 4,857,042 A | 8/1989 | Schneider |
| 4,863,593 A | 9/1989 | Quick |
| 4,867,740 A | 9/1989 | East |
| 4,874,377 A | 10/1989 | Newgard et al. |
| 4,883,474 A | 11/1989 | Sheridan et al. |
| 4,883,476 A | 11/1989 | Kurtz et al. |
| 4,921,488 A | 5/1990 | Maitz et al. |
| 4,928,830 A | 5/1990 | Brewer |
| 4,929,235 A | 5/1990 | Merry et al. |
| 4,930,997 A | 6/1990 | Bennett |
| 4,936,837 A | 6/1990 | Wexler |
| 4,944,732 A | 7/1990 | Russo |
| 4,946,448 A | 8/1990 | Richmond |
| 4,946,449 A | 8/1990 | Davis, Jr. |
| 4,949,756 A | 8/1990 | Melinyshyn et al. |
| 4,950,256 A | 8/1990 | Luther et al. |
| 4,960,412 A | 10/1990 | Fink |
| 4,966,197 A | 10/1990 | Jaron et al. |
| 4,968,294 A | 11/1990 | Salama |
| 4,969,879 A | 11/1990 | Lichte |
| 4,969,890 A | 11/1990 | Sugita et al. |
| 4,973,311 A | 11/1990 | Iwakoshi et al. |
| 4,981,474 A | 1/1991 | Bopp et al. |
| 4,995,864 A | 2/1991 | Bartholomew et al. |
| 5,002,528 A | 3/1991 | Palestrant |
| 5,002,529 A | 3/1991 | Cunningham |
| 5,009,635 A | 4/1991 | Scarberry |
| 5,009,636 A | 4/1991 | Wortley et al. |
| 5,019,059 A | 5/1991 | Goldberg et al. |
| 5,019,096 A | 5/1991 | Fox, Jr. et al. |
| 5,024,653 A | 6/1991 | Kohnka |
| 5,037,403 A | 8/1991 | Garcia |
| 5,048,875 A | 9/1991 | Usui et al. |
| 5,052,998 A | 10/1991 | Zimmon |
| 5,053,014 A | 10/1991 | Van Heugten |
| 5,057,084 A | 10/1991 | Ensminger et al. |

(56) References Cited

U.S. PATENT DOCUMENTS

| | | | |
|---|---|---|---|
| 5,060,833 A | 10/1991 | Edison et al. |
| 5,061,255 A | 10/1991 | Greenfeld et al. |
| 5,062,835 A | 11/1991 | Maitz et al. |
| 5,064,416 A | 11/1991 | Newgard et al. |
| 5,078,677 A | 1/1992 | Gentelia et al. |
| 5,078,689 A | 1/1992 | Keller |
| 5,078,699 A | 1/1992 | Haber et al. |
| 5,085,349 A | 2/1992 | Fawcett |
| 5,092,850 A | 3/1992 | Buma |
| 5,098,405 A | 3/1992 | Peterson et al. |
| 5,100,394 A | 3/1992 | Dudar et al. |
| 5,102,404 A | 4/1992 | Goldberg et al. |
| 5,106,054 A | 4/1992 | Mollenauer et al. |
| 5,112,323 A | 5/1992 | Winkler et al. |
| 5,123,677 A | 6/1992 | Kreczko et al. |
| 5,137,524 A | 8/1992 | Lynn et al. |
| 5,139,512 A | 8/1992 | Dreiling et al. |
| 5,141,499 A | 8/1992 | Zappacosta |
| 5,156,597 A | 10/1992 | Verreet et al. |
| 5,188,622 A | 2/1993 | Muller et al. |
| 5,207,655 A | 5/1993 | Sheridan |
| 5,215,538 A | 6/1993 | Larkin |
| 5,234,454 A | 8/1993 | Bangs |
| 5,238,217 A | 8/1993 | Fell |
| 5,242,422 A | 9/1993 | Schneberger et al. |
| 5,251,873 A | 10/1993 | Atkinson et al. |
| 5,261,897 A | 11/1993 | Kurtz et al. |
| 5,269,771 A | 12/1993 | Thomas et al. |
| 5,269,803 A | 12/1993 | Geary et al. |
| 5,279,551 A | 1/1994 | James |
| 5,279,601 A | 1/1994 | Lichte |
| 5,280,876 A | 1/1994 | Atkins |
| 5,295,657 A | 3/1994 | Atkinson |
| 5,295,658 A | 3/1994 | Atkinson et al. |
| 5,300,034 A | 4/1994 | Behnke et al. |
| 5,300,048 A | 4/1994 | Drewes, Jr. et al. |
| 5,304,121 A | 4/1994 | Sahatjian |
| 5,304,186 A | 4/1994 | Semler et al. |
| 5,304,201 A | 4/1994 | Rice |
| 5,309,924 A | 5/1994 | Peabody |
| 5,320,110 A | 6/1994 | Wang |
| 5,322,518 A | 6/1994 | Schneider et al. |
| 5,330,447 A | 7/1994 | Barth |
| 5,334,159 A | 8/1994 | Turkel |
| 5,334,166 A | 8/1994 | Palestrant |
| 5,344,401 A | 9/1994 | Radisch et al. |
| 5,345,929 A | 9/1994 | Jansson et al. |
| 5,352,198 A | 10/1994 | Goldenberg et al. |
| 5,356,391 A | 10/1994 | Stewart |
| 5,360,413 A | 11/1994 | Leason et al. |
| 5,390,898 A | 2/1995 | Smedley et al. |
| 5,399,165 A | 3/1995 | Paul, Jr. |
| 5,401,245 A | 3/1995 | Haining |
| 5,403,284 A | 4/1995 | Gross |
| 5,405,331 A | 4/1995 | Bahnke et al. |
| 5,407,434 A | 4/1995 | Gross |
| 5,423,334 A | 6/1995 | Jordan |
| 5,435,470 A | 7/1995 | Kim |
| 5,437,900 A | 8/1995 | Kuzowski |
| 5,456,675 A | 10/1995 | Wolbring et al. |
| 5,470,319 A | 11/1995 | Mayer |
| 5,472,325 A | 12/1995 | Svendsen |
| 5,472,435 A | 12/1995 | Sutton |
| 5,480,392 A | 1/1996 | Mous |
| 5,484,401 A | 1/1996 | Rodriguez |
| 5,489,269 A | 2/1996 | Aldrich et al. |
| 5,492,304 A | 2/1996 | Smith et al. |
| 5,496,299 A | 3/1996 | Felix et al. |
| 5,501,426 A | 3/1996 | Atkinson et al. |
| 5,505,717 A | 4/1996 | Moore |
| 5,507,733 A | 4/1996 | Larkin |
| 5,507,847 A | 4/1996 | George et al. |
| 5,509,433 A | 4/1996 | Paradis |
| 5,509,909 A | 4/1996 | Moy |
| 5,509,912 A | 4/1996 | Vaillancourt et al. |
| 5,512,056 A | 4/1996 | Stevens et al. |
| 5,514,117 A | 5/1996 | Lynn |
| 5,514,155 A | 5/1996 | Daneshvar |
| 5,520,665 A | 5/1996 | Fleetwood et al. |
| 5,529,278 A | 6/1996 | Weldon et al. |
| 5,535,785 A | 7/1996 | Werge et al. |
| 5,540,661 A | 7/1996 | Tomisaka et al. |
| 5,556,387 A | 9/1996 | Mollenauer et al. |
| 5,573,516 A | 11/1996 | Tyner |
| 5,597,536 A | 1/1997 | Mayer |
| 5,613,491 A | 3/1997 | Kanner et al. |
| 5,628,735 A | 5/1997 | Skow |
| 5,628,908 A | 5/1997 | Kamen et al. |
| 5,636,875 A | 6/1997 | Wasser et al. |
| 5,637,103 A | 6/1997 | Kerwin et al. |
| 5,662,960 A | 9/1997 | Hostettler et al. |
| 5,674,192 A | 10/1997 | Sahatjian et al. |
| 5,676,346 A | 10/1997 | Leinsing |
| D385,889 S | 11/1997 | Kullas et al. |
| 5,685,866 A | 11/1997 | Lopez |
| 5,690,612 A | 11/1997 | Lopez et al. |
| 5,695,466 A | 12/1997 | Lopez et al. |
| 5,695,520 A | 12/1997 | Bruckner et al. |
| 5,701,934 A | 12/1997 | Kuran et al. |
| 5,709,672 A | 1/1998 | Illner |
| 5,725,506 A | 3/1998 | Freeman et al. |
| 5,727,714 A | 3/1998 | Fawcett |
| 5,728,120 A | 3/1998 | Shani et al. |
| 5,733,496 A | 3/1998 | Avellanet |
| 5,735,826 A | 4/1998 | Richmond |
| 5,738,144 A | 4/1998 | Rogers |
| 5,738,656 A | 4/1998 | Wagner |
| 5,776,119 A | 7/1998 | Bilbo et al. |
| 5,779,657 A * | 7/1998 | Daneshvar ........... A61B 17/135 602/60 |
| 5,792,098 A | 8/1998 | Felix et al. |
| 5,792,108 A | 8/1998 | Felix et al. |
| 5,807,348 A | 9/1998 | Zinger et al. |
| 5,810,792 A | 9/1998 | Fangrow, Jr. et al. |
| 5,814,024 A | 9/1998 | Thompson et al. |
| 5,823,961 A | 10/1998 | Fields et al. |
| 5,830,185 A | 11/1998 | Block, Jr. |
| 5,839,715 A | 11/1998 | Leinsing |
| 5,873,853 A | 2/1999 | Keilman et al. |
| 5,897,782 A | 4/1999 | Chatelin et al. |
| 5,904,334 A | 5/1999 | Grunert et al. |
| 5,921,972 A | 7/1999 | Skow |
| 5,937,885 A | 8/1999 | Sampson |
| 5,938,176 A | 8/1999 | Falconer |
| 5,944,703 A | 8/1999 | Dixon et al. |
| 5,947,953 A | 9/1999 | Ash et al. |
| 5,954,313 A | 9/1999 | Ryan |
| 5,954,706 A | 9/1999 | Sahatjian |
| 5,957,898 A | 9/1999 | Jepson et al. |
| 5,957,912 A | 9/1999 | Heitzmann |
| 5,961,497 A | 10/1999 | Larkin |
| 5,971,357 A | 10/1999 | Denton et al. |
| 5,972,441 A | 10/1999 | Campbell et al. |
| 5,976,650 A | 11/1999 | Campbell et al. |
| 5,984,891 A | 11/1999 | Keilman et al. |
| 5,997,486 A | 12/1999 | Burek et al. |
| 5,997,564 A | 12/1999 | Shehata et al. |
| 6,001,079 A | 12/1999 | Pourchez |
| 6,024,731 A | 2/2000 | Seddon et al. |
| 6,025,044 A | 2/2000 | Campbell et al. |
| 6,027,779 A | 2/2000 | Campbell et al. |
| 6,027,811 A | 2/2000 | Campbell et al. |
| 6,029,946 A | 2/2000 | Doyle |
| 6,039,302 A | 3/2000 | Cote, Sr. et al. |
| 6,039,714 A | 3/2000 | Cracauer et al. |
| 6,056,730 A | 5/2000 | Greter |
| 6,056,731 A | 5/2000 | Koetke et al. |
| 6,063,062 A | 5/2000 | Paradis |
| 6,068,011 A | 5/2000 | Paradis |
| 6,068,646 A | 5/2000 | Lam |
| 6,070,767 A | 6/2000 | Gardner et al. |
| 6,079,444 A | 6/2000 | Harris et al. |
| 6,089,541 A | 7/2000 | Weinheimer et al. |
| 6,093,154 A | 7/2000 | Burek et al. |

(56) References Cited

U.S. PATENT DOCUMENTS

| | | |
|---|---|---|
| 6,103,695 A | 8/2000 | Lane et al. |
| 6,106,502 A | 8/2000 | Richmond |
| 6,106,503 A | 8/2000 | Pfeiderer et al. |
| 6,113,068 A | 9/2000 | Ryan |
| 6,117,114 A | 9/2000 | Paradis |
| 6,120,264 A | 9/2000 | Wang |
| 6,129,699 A | 10/2000 | Haight et al. |
| 6,129,750 A | 10/2000 | Tockman et al. |
| 6,132,403 A | 10/2000 | Lopez |
| 6,132,407 A | 10/2000 | Genese et al. |
| 6,149,129 A | 11/2000 | Harris et al. |
| 6,156,004 A | 12/2000 | Tremaine et al. |
| 6,165,217 A | 12/2000 | Hayes |
| 6,168,137 B1 | 1/2001 | Paradis |
| 6,170,800 B1 | 1/2001 | Meloul et al. |
| 6,171,287 B1 | 1/2001 | Lynn et al. |
| 6,193,682 B1 | 2/2001 | Ahmed |
| 6,196,992 B1 | 3/2001 | Keilman et al. |
| 6,200,292 B1 | 3/2001 | French et al. |
| 6,217,556 B1 | 4/2001 | Ellingson et al. |
| 6,221,425 B1 | 4/2001 | Michal et al. |
| 6,231,507 B1 | 5/2001 | Zikorus et al. |
| 6,234,992 B1 | 5/2001 | Haight et al. |
| 6,234,996 B1 | 5/2001 | Bagaoisan et al. |
| 6,235,009 B1 | 5/2001 | Skow |
| 6,245,048 B1 | 6/2001 | Fangrow, Jr. et al. |
| 6,254,061 B1 | 7/2001 | Levine et al. |
| 6,254,581 B1 | 7/2001 | Scott |
| 6,261,276 B1 | 7/2001 | Reitsma |
| 6,261,282 B1 | 7/2001 | Jepson et al. |
| 6,283,949 B1 | 9/2001 | Roorda |
| 6,287,285 B1 | 9/2001 | Michal et al. |
| 6,293,929 B1 | 9/2001 | Smith et al. |
| 6,299,131 B1 | 10/2001 | Ryan |
| 6,299,593 B1 | 10/2001 | Wakabayashi |
| 6,319,235 B1 | 11/2001 | Yoshimo |
| 6,328,765 B1 | 12/2001 | Hardwick et al. |
| 6,332,892 B1 | 12/2001 | Desmond, III et al. |
| 6,344,033 B1 | 2/2002 | Jepson et al. |
| 6,352,525 B1 | 3/2002 | Wakabayashi |
| 6,375,024 B1 | 4/2002 | Park |
| 6,391,009 B1 | 5/2002 | Crosa Dorado |
| 6,409,716 B1 | 6/2002 | Sahatjian et al. |
| 6,428,520 B1 | 8/2002 | Lopez et al. |
| 6,447,473 B1 | 9/2002 | Levine et al. |
| 6,482,190 B1 | 11/2002 | Genese et al. |
| 6,491,668 B1 | 12/2002 | Paradis |
| 6,500,164 B1 | 12/2002 | Turner et al. |
| 6,530,951 B1 | 3/2003 | Bates et al. |
| 6,541,116 B2 | 4/2003 | Michal et al. |
| 6,551,267 B1 | 4/2003 | Cohen et al. |
| 6,554,808 B1 | 4/2003 | Cook |
| 6,562,013 B1 | 5/2003 | Marasco, Jr. |
| RE38,145 E | 6/2003 | Lynn |
| 6,620,132 B1 | 9/2003 | Skow |
| 6,626,418 B2 | 9/2003 | Kiehne et al. |
| 6,629,707 B1 | 10/2003 | Yamaguchi et al. |
| 6,634,384 B2 | 10/2003 | Skeens et al. |
| 6,635,020 B2 | 10/2003 | Tripp, Jr. et al. |
| 6,637,726 B1 | 10/2003 | Yamamoto |
| 6,641,562 B1 | 11/2003 | Peterson |
| 6,641,574 B2 | 11/2003 | Badia Segura et al. |
| 6,645,547 B1 | 11/2003 | Shekalim et al. |
| 6,647,986 B1 | 11/2003 | Korotko et al. |
| 6,651,956 B2 | 11/2003 | Miller |
| 6,652,484 B1 | 11/2003 | Hunckler et al. |
| 6,655,655 B1 | 12/2003 | Matkovich et al. |
| 6,656,517 B2 | 12/2003 | Michal et al. |
| 6,669,681 B2 | 12/2003 | Jepson et al. |
| 6,673,049 B2 | 1/2004 | Hommann et al. |
| 6,673,051 B2 | 1/2004 | Flinchbaugh |
| 6,695,817 B1 | 2/2004 | Fangrow, Jr. |
| 6,706,022 B2 | 3/2004 | Leinsing et al. |
| 6,708,950 B2 | 3/2004 | Christensen et al. |
| 6,719,991 B2 | 4/2004 | Darouiche et al. |
| 6,726,672 B1 | 4/2004 | Hanly et al. |
| 6,730,107 B2 | 5/2004 | Kelley et al. |
| 6,733,000 B2 | 5/2004 | Mccarty et al. |
| 6,733,481 B2 | 5/2004 | Ow |
| 6,745,998 B2 | 6/2004 | Doyle |
| 6,755,391 B2 | 6/2004 | Newton et al. |
| 6,780,497 B1 | 8/2004 | Walter |
| 6,802,836 B2 | 10/2004 | Bouphavichith et al. |
| 6,808,161 B1 | 10/2004 | Hishikawa |
| D500,132 S | 12/2004 | Peterson et al. |
| D500,133 S | 12/2004 | Peterson et al. |
| 6,833,001 B1 | 12/2004 | Chao |
| D500,552 S | 1/2005 | Peterson et al. |
| D500,853 S | 1/2005 | Peterson et al. |
| 6,840,501 B2 | 1/2005 | Doyle |
| 6,849,061 B2 | 2/2005 | Wagner |
| 6,896,665 B2 | 5/2005 | Picha et al. |
| 6,897,349 B2 | 5/2005 | Gibbins et al. |
| 6,916,379 B2 | 7/2005 | Shekalim et al. |
| 6,936,031 B2 | 8/2005 | Caleffi |
| 6,972,001 B2 | 12/2005 | Emig et al. |
| 6,994,315 B2 | 2/2006 | Ryan et al. |
| 7,004,923 B2 | 2/2006 | Deniega et al. |
| 7,004,934 B2 | 2/2006 | Vaillancourt |
| 7,008,407 B1 | 3/2006 | Kamp |
| 7,044,441 B2 | 5/2006 | Doyle |
| 7,048,724 B2 | 5/2006 | Grossman et al. |
| 7,048,962 B2 | 5/2006 | Shekalim et al. |
| 7,052,603 B2 | 5/2006 | Schick |
| 7,090,191 B2 | 8/2006 | Matkovich et al. |
| 7,094,218 B2 | 8/2006 | Rome et al. |
| 7,100,890 B2 | 9/2006 | Cote, Sr. et al. |
| 7,101,353 B2 | 9/2006 | Lui et al. |
| 7,112,177 B2 | 9/2006 | Christensen et al. |
| 7,150,740 B2 | 12/2006 | Bennett et al. |
| 7,163,495 B2 | 1/2007 | Fazio et al. |
| 7,165,568 B2 | 1/2007 | Kessell et al. |
| 7,179,244 B2 | 2/2007 | Smith et al. |
| 7,184,825 B2 | 2/2007 | Leinsing et al. |
| 7,207,946 B2 | 4/2007 | Sirokman |
| 7,303,553 B2 | 12/2007 | Ott |
| 7,311,690 B2 | 12/2007 | Burnett |
| 7,314,061 B2 | 1/2008 | Peppel |
| 7,320,674 B2 | 1/2008 | Ruddell et al. |
| 7,341,240 B2 | 3/2008 | Ciesielka |
| 7,377,915 B2 | 5/2008 | Rasmussen et al. |
| 7,396,348 B2 | 7/2008 | Newton et al. |
| 7,401,703 B2 | 7/2008 | Mcmichael et al. |
| 7,452,346 B2 | 11/2008 | Axelsson |
| 7,452,354 B2 | 11/2008 | Bright et al. |
| 7,468,058 B2 | 12/2008 | Kanie et al. |
| 7,497,848 B2 | 3/2009 | Leinsing et al. |
| 7,497,849 B2 | 3/2009 | Fangrow, Jr. |
| 7,524,311 B2 | 4/2009 | Phung et al. |
| 7,530,546 B2 | 5/2009 | Ryan et al. |
| 7,547,302 B2 | 6/2009 | Porto et al. |
| 7,563,243 B2 | 7/2009 | Mendels |
| 7,569,045 B2 | 8/2009 | Deniega et al. |
| 7,578,803 B2 | 8/2009 | Rome et al. |
| 7,584,767 B2 | 9/2009 | Funamura et al. |
| 7,591,805 B2 | 9/2009 | Lampropoulos |
| 7,594,910 B2 | 9/2009 | Butts et al. |
| 7,611,503 B2 | 11/2009 | Spohn et al. |
| 7,614,123 B2 | 11/2009 | Schweikert |
| 7,621,903 B2 | 11/2009 | Delegge |
| 7,628,774 B2 | 12/2009 | Fangrow, Jr. |
| 7,628,779 B2 | 12/2009 | Aneas |
| 7,632,260 B2 | 12/2009 | Antoine |
| 7,637,893 B2 | 12/2009 | Christensen et al. |
| 7,644,722 B2 | 1/2010 | Christensen et al. |
| 7,674,248 B2 | 3/2010 | Anderson et al. |
| 7,678,092 B2 | 3/2010 | Matloub et al. |
| 7,682,332 B2 | 3/2010 | Tanaka |
| 7,691,090 B2 | 4/2010 | Belley et al. |
| 7,695,458 B2 | 4/2010 | Belley et al. |
| 7,708,027 B2 | 5/2010 | Yokota et al. |
| 7,717,891 B1 | 5/2010 | Whaley |
| 7,726,315 B2 | 6/2010 | Field |
| 7,726,328 B2 | 6/2010 | Christensen et al. |

(56) References Cited

U.S. PATENT DOCUMENTS

| | | |
|---|---|---|
| 7,736,336 B2 | 6/2010 | Plilshka et al. |
| 7,744,594 B2 | 6/2010 | Yamazaki et al. |
| 7,758,574 B2 | 7/2010 | Hijii et al. |
| 7,766,304 B2 | 8/2010 | Phillips |
| 7,766,938 B2 | 8/2010 | Mcgurk et al. |
| 7,780,612 B2 | 8/2010 | Ross |
| 7,798,974 B2 | 9/2010 | Sirokman |
| 7,815,168 B2 | 10/2010 | Vangsness et al. |
| 7,824,384 B2 | 11/2010 | Watson, Jr. |
| 7,833,194 B2 | 11/2010 | Owens et al. |
| 7,854,731 B2 | 12/2010 | Rome et al. |
| 7,857,284 B2 | 12/2010 | Kimball et al. |
| 7,867,204 B2 | 1/2011 | Bartholomew et al. |
| 7,879,012 B2 | 2/2011 | Kane et al. |
| 7,892,181 B2 | 2/2011 | Christensen et al. |
| 8,007,257 B2 | 8/2011 | Heaton et al. |
| 8,048,046 B2 | 11/2011 | Hudspeth et al. |
| 8,048,056 B2 | 11/2011 | Picha et al. |
| 8,052,671 B2 | 11/2011 | Christensen et al. |
| 8,057,448 B2 | 11/2011 | Williams et al. |
| 8,074,848 B2 | 12/2011 | Pittl et al. |
| 8,083,332 B2 | 12/2011 | Price et al. |
| 8,147,417 B2 | 4/2012 | Gavriely |
| 8,177,772 B2 | 5/2012 | Christensen et al. |
| 8,210,166 B2 | 7/2012 | Denton et al. |
| 8,224,422 B2 | 7/2012 | Mottola et al. |
| 8,235,971 B2 | 8/2012 | Christensen et al. |
| 8,246,590 B2 | 8/2012 | Hu et al. |
| 8,337,475 B2 | 12/2012 | Christensen et al. |
| 8,435,221 B2 | 5/2013 | Hu et al. |
| 8,632,840 B2 | 1/2014 | Avitable |
| 8,636,721 B2 | 1/2014 | Alam et al. |
| 8,814,839 B2 | 8/2014 | Christensen et al. |
| 8,845,680 B2 | 9/2014 | Lampropoulos et al. |
| 9,295,764 B2 | 3/2016 | Christensen et al. |
| 9,332,994 B2 | 5/2016 | Pancholy et al. |
| 9,393,353 B2 | 7/2016 | Alam et al. |
| D804,663 S | 12/2017 | Jenkins |
| D821,590 S | 6/2018 | Hylton et al. |
| 10,172,625 B2 | 1/2019 | Wada et al. |
| 10,463,833 B2 | 11/2019 | Clarke et al. |
| 10,492,797 B2 | 12/2019 | Okamura |
| D893,034 S | 8/2020 | Kase et al. |
| 2001/0047158 A1 | 11/2001 | Ladd |
| 2002/0002351 A1 | 1/2002 | Cote et al. |
| 2002/0123715 A1 | 9/2002 | Sorenson et al. |
| 2002/0148467 A1 | 10/2002 | Bosse et al. |
| 2002/0153503 A1 | 10/2002 | Newton et al. |
| 2002/0188315 A1 | 12/2002 | Guzman et al. |
| 2002/0198458 A1 | 12/2002 | Tripp et al. |
| 2003/0017920 A1 | 1/2003 | Fazio et al. |
| 2003/0032940 A1 | 2/2003 | Doyle |
| 2003/0040769 A1 | 2/2003 | Kelley et al. |
| 2003/0055453 A1 | 3/2003 | Akerfeldt |
| 2003/0062498 A1 | 4/2003 | Decler et al. |
| 2003/0111121 A1 | 6/2003 | Skeens et al. |
| 2003/0139766 A1 | 7/2003 | Mcewen et al. |
| 2003/0149359 A1 | 8/2003 | Smith |
| 2003/0159755 A1 | 8/2003 | Wessberg |
| 2003/0165647 A1 | 9/2003 | Kaneko et al. |
| 2003/0173536 A1 | 9/2003 | Christensen et al. |
| 2004/0049157 A1 | 3/2004 | Plishka et al. |
| 2004/0078026 A1 | 4/2004 | Wagner |
| 2004/0082923 A1 | 4/2004 | Field |
| 2004/0116894 A1 | 6/2004 | Delegge |
| 2004/0215155 A1 | 10/2004 | Wolfe et al. |
| 2004/0232696 A1 | 11/2004 | Andre |
| 2004/0267163 A1 | 12/2004 | Opie et al. |
| 2005/0025816 A1 | 2/2005 | Tanaka |
| 2005/0090805 A1 | 4/2005 | Shaw et al. |
| 2005/0113866 A1 | 5/2005 | Heinz et al. |
| 2005/0121638 A1 | 6/2005 | Doyle |
| 2005/0125025 A1* | 6/2005 | Rioux ............... A61B 17/1325 606/157 |
| 2005/0131321 A1* | 6/2005 | Ravikumar ............ B32B 27/12 601/152 |
| 2005/0131357 A1 | 6/2005 | Denton et al. |
| 2005/0143691 A1 | 6/2005 | Picha et al. |
| 2005/0203463 A1 | 9/2005 | Lampropoulos |
| 2005/0203597 A1 | 9/2005 | Yamazaki et al. |
| 2005/0209572 A1 | 9/2005 | Rome et al. |
| 2005/0209581 A1 | 9/2005 | Butts et al. |
| 2005/0251102 A1 | 11/2005 | Hegland et al. |
| 2005/0261636 A1 | 11/2005 | Rome et al. |
| 2005/0261664 A1 | 11/2005 | Rome et al. |
| 2005/0267445 A1 | 12/2005 | Mendels |
| 2005/0267487 A1 | 12/2005 | Christensen et al. |
| 2005/0281822 A1 | 12/2005 | Cedarbaum et al. |
| 2006/0009801 A1 | 1/2006 | Mcgurk et al. |
| 2006/0015086 A1 | 1/2006 | Rasmussen et al. |
| 2006/0058702 A1 | 3/2006 | Christensen et al. |
| 2006/0058841 A1 | 3/2006 | Mills et al. |
| 2006/0079853 A1 | 4/2006 | Christensen et al. |
| 2006/0116721 A1 | 6/2006 | Yun et al. |
| 2006/0118749 A1 | 6/2006 | Ryan et al. |
| 2006/0129109 A1 | 6/2006 | Shaw et al. |
| 2006/0190026 A1 | 8/2006 | Sanders |
| 2006/0200089 A1 | 9/2006 | Lopez et al. |
| 2006/0211998 A1 | 9/2006 | Fangrow |
| 2006/0211999 A1 | 9/2006 | Fangrow |
| 2006/0212000 A1 | 9/2006 | Fangrow |
| 2006/0212001 A1 | 9/2006 | Fangrow |
| 2006/0212002 A1 | 9/2006 | Fangrow |
| 2006/0212003 A1 | 9/2006 | Fangrow |
| 2006/0264842 A1 | 11/2006 | Fangrow |
| 2007/0038143 A1 | 2/2007 | Christensen et al. |
| 2007/0073270 A1 | 3/2007 | Christensen et al. |
| 2007/0083157 A1 | 4/2007 | Belley et al. |
| 2007/0083162 A1 | 4/2007 | O'Reagan et al. |
| 2007/0100295 A1 | 5/2007 | Belley et al. |
| 2007/0100322 A1 | 5/2007 | Venugopalan et al. |
| 2007/0100324 A1 | 5/2007 | Tempel et al. |
| 2007/0235674 A1 | 10/2007 | Vangsness et al. |
| 2007/0235675 A1 | 10/2007 | Kimball et al. |
| 2007/0235676 A1 | 10/2007 | Vangsness et al. |
| 2007/0239092 A1 | 10/2007 | Ross |
| 2007/0248810 A1 | 10/2007 | Mcgee et al. |
| 2007/0255167 A1 | 11/2007 | Christensen et al. |
| 2007/0255229 A1 | 11/2007 | Kane et al. |
| 2007/0260195 A1 | 11/2007 | Bartholomew et al. |
| 2007/0270720 A1 | 11/2007 | Fry |
| 2007/0270764 A1 | 11/2007 | Gordon |
| 2007/0282268 A1 | 12/2007 | Mayse |
| 2008/0097407 A1 | 2/2008 | Plishka |
| 2008/0091174 A1 | 4/2008 | Alam et al. |
| 2008/0103408 A1 | 5/2008 | Denton et al. |
| 2008/0114316 A1 | 5/2008 | Christensen et al. |
| 2008/0177175 A1 | 7/2008 | Mottola et al. |
| 2008/0277610 A1 | 11/2008 | Bahner et al. |
| 2009/0012493 A1 | 1/2009 | Harig |
| 2009/0043270 A1 | 2/2009 | Noyce et al. |
| 2009/0062843 A1* | 3/2009 | Heston ............... A61B 17/1322 606/203 |
| 2009/0069763 A1 | 3/2009 | Dicarlo et al. |
| 2009/0142741 A1 | 6/2009 | Ault et al. |
| 2009/0209896 A1 | 8/2009 | Selevan |
| 2009/0219353 A1 | 9/2009 | Price et al. |
| 2009/0240182 A1 | 9/2009 | Weber et al. |
| 2009/0261130 A1 | 10/2009 | Pittl et al. |
| 2009/0281565 A1 | 11/2009 | Mcneese |
| 2009/0312725 A1 | 12/2009 | Braga |
| 2009/0314973 A1 | 12/2009 | Christensen et al. |
| 2010/0030163 A1 | 2/2010 | Carrez et al. |
| 2010/0044609 A1 | 2/2010 | Matsubara |
| 2010/0211000 A1 | 8/2010 | Killion et al. |
| 2010/0217202 A1 | 8/2010 | Clark |
| 2010/0274229 A1 | 10/2010 | Duocastella Codina et al. |
| 2010/0280541 A1 | 11/2010 | Lampropoulos |
| 2011/0009849 A1 | 1/2011 | Christensen et al. |
| 2011/0022012 A1 | 1/2011 | Kerr et al. |
| 2011/0071415 A1 | 3/2011 | Karwoski et al. |
| 2011/0083665 A1 | 4/2011 | Denton et al. |
| 2011/0105963 A1 | 5/2011 | Hu et al. |

(56) References Cited

U.S. PATENT DOCUMENTS

| | | |
|---|---|---|
| 2011/0172510 A1 | 7/2011 | Chickering, III |
| 2011/0238022 A1 | 9/2011 | Massi et al. |
| 2011/0275964 A1 | 11/2011 | Greener |
| 2011/0276017 A1 | 11/2011 | Schuessler et al. |
| 2012/0089109 A1 | 4/2012 | Turner et al. |
| 2012/0220984 A1 | 8/2012 | Christensen et al. |
| 2012/0221041 A1 | 8/2012 | Hansson et al. |
| 2012/0238934 A1 | 9/2012 | During |
| 2012/0296369 A1 | 11/2012 | Atthoff et al. |
| 2013/0023734 A1 | 1/2013 | Okamura |
| 2013/0079723 A1 | 3/2013 | Andino et al. |
| 2013/0090614 A1 | 4/2013 | Christensen et al. |
| 2013/0165787 A1 | 6/2013 | Ukawa et al. |
| 2013/0237866 A1 | 9/2013 | Cohen |
| 2013/0245675 A1 | 9/2013 | Wada et al. |
| 2013/0289613 A1 | 10/2013 | Wada et al. |
| 2014/0012120 A1 | 1/2014 | Cohen et al. |
| 2014/0012313 A1 | 1/2014 | Finkielsztien et al. |
| 2014/0142615 A1 | 5/2014 | Corrigan, Jr. |
| 2014/0182594 A1 | 7/2014 | Alam et al. |
| 2014/0236221 A1 | 8/2014 | Zhadkevich |
| 2014/0288408 A1 | 9/2014 | Deutsch |
| 2014/0358095 A1 | 12/2014 | Christensen et al. |
| 2015/0018868 A1 | 1/2015 | Pancholy |
| 2015/0018869 A1 | 1/2015 | Benz et al. |
| 2015/0032149 A1 | 1/2015 | Croushorn et al. |
| 2015/0164436 A1 | 6/2015 | Maron et al. |
| 2015/0201948 A1 | 7/2015 | Kornowski et al. |
| 2015/0314074 A1 | 11/2015 | Howlett et al. |
| 2015/0327870 A1 | 11/2015 | Fortson et al. |
| 2015/0327871 A1 | 11/2015 | Fortson et al. |
| 2015/0342615 A1 | 12/2015 | Keinan et al. |
| 2016/0058988 A1 | 3/2016 | Kesten et al. |
| 2016/0101269 A1 | 4/2016 | Benz |
| 2016/0183951 A1 | 6/2016 | Pancholy |
| 2016/0279395 A1 | 9/2016 | Lampropoulos et al. |
| 2017/0000988 A1 | 1/2017 | Stevens et al. |
| 2017/0007807 A1 | 1/2017 | Weerakoon et al. |
| 2017/0273693 A1 | 9/2017 | Morrison et al. |
| 2018/0000494 A1 | 1/2018 | Wada et al. |
| 2018/0008281 A1 | 1/2018 | Hazama |
| 2018/0008282 A1 | 1/2018 | Hazama et al. |
| 2018/0008283 A1 | 1/2018 | Hazama |
| 2018/0014832 A1 | 1/2018 | Lampropoulos et al. |
| 2018/0028195 A1 | 2/2018 | Benz et al. |
| 2018/0042615 A1 | 2/2018 | Kimura et al. |
| 2018/0070956 A1 | 3/2018 | Lampropoulos et al. |
| 2018/0185032 A1 | 7/2018 | Matsushita et al. |
| 2018/0250017 A1 | 9/2018 | Matsushita et al. |
| 2018/0280008 A1 | 10/2018 | Okamura |
| 2019/0021742 A1 | 1/2019 | Hazama |
| 2019/0029693 A1 | 1/2019 | Okamura |
| 2019/0046214 A1 | 2/2019 | Hazama |
| 2019/0090886 A1 | 3/2019 | Brown et al. |
| 2019/0133602 A1 | 5/2019 | Kiemeneij et al. |
| 2019/0133604 A1 | 5/2019 | Maeda et al. |
| 2019/0133605 A1 | 5/2019 | Hazama et al. |
| 2019/0133606 A1 | 5/2019 | Hazama |
| 2019/0133607 A1 | 5/2019 | Hazama |
| 2019/0150938 A1 | 5/2019 | Hazama et al. |
| 2019/0167273 A1 | 6/2019 | Morrison et al. |
| 2019/0274692 A1 | 9/2019 | Lampropoulos et al. |
| 2019/0290288 A1 | 9/2019 | Popp |
| 2019/0314035 A1 | 10/2019 | Hopkinson et al. |
| 2020/0029946 A1 | 1/2020 | Green et al. |
| 2020/0390469 A1 | 12/2020 | Hoffman et al. |
| 2020/0390496 A1 | 12/2020 | Houden et al. |
| 2021/0052282 A1 | 2/2021 | Lampropoulos et al. |
| 2022/0047272 A1 | 2/2022 | Hopkinson et al. |
| 2022/0370080 A1 | 11/2022 | Kiemeneij et al. |
| 2022/0401086 A1 | 12/2022 | Stephenson et al. |

FOREIGN PATENT DOCUMENTS

| | | |
|---|---|---|
| CN | 201861701 | 6/2011 |
| CN | 208864401 | 5/2019 |
| CN | 209695299 | 11/2019 |
| DE | 1616493 | 6/1971 |
| DE | 4006696 | 11/1990 |
| DE | 9105229 | 6/1991 |
| DE | 4311715 | 10/1994 |
| EP | 0270205 | 6/1988 |
| EP | 0829248 | 3/1998 |
| EP | 1547537 | 6/2005 |
| EP | 1740253 | 1/2007 |
| EP | 1782850 | 5/2007 |
| FR | 2551978 | 3/1985 |
| FR | 2828231 | 2/2003 |
| GB | 2109239 | 6/1983 |
| GB | 2394761 | 5/2004 |
| JP | 2002049660 | 2/1990 |
| JP | 2005115556 | 5/1993 |
| JP | H6504468 | 5/1994 |
| JP | H666642 | 9/1994 |
| JP | 1995047071 | 2/1995 |
| JP | 2000517216 | 12/2000 |
| JP | 2002177379 | 6/2002 |
| JP | 2012010823 | 1/2012 |
| JP | 2013042859 | 3/2013 |
| JP | 2013111444 | 6/2013 |
| JP | 6211285 | 10/2014 |
| JP | 2014200308 | 10/2014 |
| JP | 6261368 | 8/2015 |
| JP | 2015150298 | 8/2015 |
| JP | 6389510 | 9/2015 |
| JP | 6261420 | 11/2015 |
| JP | 2015188608 | 11/2015 |
| JP | 2017000259 | 1/2017 |
| JP | 2017000260 | 1/2017 |
| JP | 2017047036 | 3/2017 |
| JP | 2018011798 | 1/2018 |
| JP | 2018011867 | 1/2018 |
| JP | 2018019927 | 2/2018 |
| JP | 2018033602 | 3/2018 |
| JP | 2018075257 | 5/2018 |
| JP | 2018171081 | 11/2018 |
| JP | 2019047956 | 3/2019 |
| JP | 2019058498 | 4/2019 |
| JP | 6544854 | 6/2019 |
| JP | 6559128 | 7/2019 |
| JP | 2019154915 | 9/2019 |
| JP | 2019166265 | 10/2019 |
| JP | 2019208953 | 12/2019 |
| JP | 2019216947 | 12/2019 |
| JP | 2019217130 | 12/2019 |
| JP | 2020014588 | 1/2020 |
| JP | 6667234 | 2/2020 |
| JP | 2020018686 | 2/2020 |
| JP | 2020022679 | 2/2020 |
| JP | 2020039815 | 3/2020 |
| JP | 2020039816 | 3/2020 |
| KR | 20140121247 A | 10/2014 |
| WO | 1990003194 | 4/1990 |
| WO | 1992007591 | 5/1992 |
| WO | 1995001135 | 1/1995 |
| WO | 199855072 | 12/1998 |
| WO | 1999011192 | 3/1999 |
| WO | 200204065 | 1/2002 |
| WO | 2003001993 | 1/2003 |
| WO | 2003018105 | 3/2003 |
| WO | 2004041313 | 5/2004 |
| WO | 2005007213 | 1/2005 |
| WO | 2005044716 | 5/2005 |
| WO | 2005052366 | 6/2005 |
| WO | 2005099805 | 10/2005 |
| WO | 2005107843 | 11/2005 |
| WO | 2006004943 | 1/2006 |
| WO | 2006055288 | 5/2006 |
| WO | 2006060248 | 6/2006 |
| WO | 2006066023 | 6/2006 |
| WO | 2007038643 | 4/2007 |

(56) References Cited

FOREIGN PATENT DOCUMENTS

| WO | 2007116386 | 10/2007 |
|---|---|---|
| WO | 2008115439 | 9/2008 |
| WO | 2008142580 | 11/2008 |
| WO | 2009027665 | 3/2009 |
| WO | 2009081180 | 7/2009 |
| WO | 2009118521 | 10/2009 |
| WO | 2010028044 | 3/2010 |
| WO | 2010091356 | 8/2010 |
| WO | 2011107972 A1 | 9/2011 |
| WO | 2015141786 | 9/2015 |
| WO | 2016118695 | 7/2016 |
| WO | 2017043536 | 3/2017 |
| WO | 2018017365 | 1/2018 |

OTHER PUBLICATIONS

Office Action dated Aug. 1, 2012 for U.S. Appl. No. 13/469,849.
Office Action dated Aug. 17, 2012 for U.S. Appl. No. 12/349,405.
Office Action dated Aug. 23, 2011 for U.S. Appl. No. 12/879,673.
Office Action dated Sep. 6, 2019 for U.S. Appl. No. 15/705,759.
Office Action dated Sep. 14, 2021 for U.S. Appl. No. 16/921,343.
Office Action dated Sep. 16, 2020 for U.S. Appl. No. 16/380,505.
Office Action dated Sep. 18, 2015 for U.S. Appl. No. 14/464,503.
Office Action dated Oct. 1, 2010 for U.S. Appl. No. 10/595,450.
Office Action dated Oct. 6, 2015 for U.S. Appl. No. 12/188,955.
Office Action dated Oct. 8, 2020 for U.S. Appl. No. 16/179,257.
Office Action dated Oct. 10, 2018 for U.S. Appl. No. 15/912,244.
Office Action dated Oct. 12, 2010 for U.S. Appl. No. 11/535,245.
Office Action dated Oct. 30, 2008 for U.S. Appl. No. 10/595,450.
Office Action dated Oct. 30, 2008 for U.S. Appl. No. 11/248,082.
Office Action dated Oct. 30, 2015 for U.S. Appl. No. 14/162,654.
Office Action dated Nov. 3, 2015 for U.S. Appl. No. 14/033,177.
Office Action dated Nov. 6, 2013 for U.S. Appl. No. 12/188,955.
Office Action dated Dec. 8, 2011 for U.S. Appl. No. 12/349,405.
Office Action dated Dec. 10, 2014 for U.S. Appl. No. 12/188,955.
Office Action dated Dec. 21, 2010 for U.S. Appl. No. 11/248,082.
Office Action dated Dec. 24, 2013 for U.S. Appl. No. 13/688,000.
Office Action dated Dec. 27, 2016 for U.S. Appl. No. 14/033,177.
Office Action dated Jul. 7, 2011 for U.S. Appl. No. 11/535,245.
"AstraTech Healthcare, 'Premimun Wound Drainage Products', http://surgery.astratech.com/Main.aspx?Item-155788&navl=5&navl=82118&nava=81296", Copyright, Jan. 1, 2010.
"Bard Access Systems, Inc., 'Poly Per-Q-Cath PICC Catheter with Safety Excalibur Introducer', Instructions for Use", May 1, 2003.
"Bard, 'Groshong Nxt Picc Instructions for Use', Product Brochure", Nov. 1, 2003.
"ICU-USA, 'Wound Drainage', www.icu-usa.com/tour/procedures/drains.htm", Copyright 1999-2004.
"Management of Malignant Pleural Effusions", Am. J. Respir. Crit. Care Med., vol. 165 No. 5, Jan. 1, 2000, 1987-2001.
"Merit Medical Adds 2 New Products for Assisting Hemostasis", Posted at Merit.com, no posting date, retrieved Aug. 26, 2020 online https://www.merit.com/articles/merit-medical-adds-2-new-products-assisting-hemostasis (2020).
"Pleural Disease-Diagnosis and Management", The Practitioner, May 1, 1999, 412.
"Pleurodesis", ASAP, vol. 118, No. 3, Sep. 1, 2000, 577.
Bellamy, "The Causes of Death in Conventional Land Warfare: Implications for combat Casualty Care Research", Mil. Med., vol. 149, Jan. 1, 1984, 55-62.
Bilski, et al., "Battlefield Casualties Treated at Camp Rhino, Afghanistan: Lessons Learned", J. Trauma, vol. 54 No. 5, May 1, 2003, 814-822.
Campisi, et al., "Outpatient Treatment of Spontaneous Pneumothorax in a Community Hospital Using a Heimlich Flutter Valve: A Case Series", The Journal of Emergency Medicine, vol. 15 No. 1, Jan. 1, 1997, 115-119.
Groves Jr., "Operations in Urban Environments", Military Review, vol. 78 No. 4.
Heimlich, "Valve Drainage of the Pleural Cavity", Diseases of the Chest, vol. 53 No. 3, Jan. 1, 1968, 282-287.
Hewitt, et al., "A Management Strategy for Malignancy-Induced Pleural Effusion: Long-Term Thoracostomy Drainage", ONF, vol. 14 No. 5, Jan. 1, 1987, 17-22.
Jaskille, et al., "A Portable Handpump is Effective inthe Evacuation of Hemothorax in a Swine Model of Penetratine Chest Injury", The Journal of Trauma Injury, Infection, and Critical Care, Nov. 1, 2003, 864-868.
Light, R.W., et al., "A Single Intrapleural Injection of Transforming Growth Factor-Beta(2) Produces an Excellent Pleurodesis in Rabbits", Am. J. Respir. Crit. Care Med., vol. 162 No. 1, Jan. 1, 2000, 98-104.
Light, et al., "Talc Slurry is an Effective Pleural Sclerosant in Rabbits", Chest, vol. 106 No. 6, Jan. 1, 1995, 1702-1706.
Lodi, et al., "A New Portable Chest Drainage Device", Ann, Thorac. Surg., vol. 69, Jan. 1, 2000, 998-1001.
Mabry, et al., "United States Army Rangers in Somalia: An Analysis of Combat Casualties on an Urban Battlefield", J. Trauma, vol. 49 No. 3, Sep. 1, 2000, 515-529.
Medcompare, "Drains with Reservoirs", General Surgery Product Matrix, Medcompare.com/matrix/1885/Drains-with-Reservoirs.html, Copyright, 198-202.
Milton Jr., "Urban Operations: Future War", Military Review, vol. 74 Issue 2, Feb. 1, 1994
Montes, et al., "Influence of Talc Dos on Extrapleural Talc Dissemination after Talc Pleurodesis", Am. J. Respir, Crit. Care Med., vol. 168 No. 3, Jan. 1, 2003, 348-355.
OHM, "Use of Indwelling Pleural Catheter Compared with Thorascopic Talc Pleurodesis in the Management of Malignant Pleural Effusions", Division of Thoracic Surgery and Department of Surgery, William Beaumont Hospital, The American Surgeon, vol. 69, Mar. 1, 2003, 198-202.
Pope, et al., "Fluid Resuscitation: State fo the Science for Treating Combat Casualties and Civilian Injuries", National Academy Press, Jan. 1, 1999.
Pua, et al., ""Snuffbox" Distal Radial Access", J Vasc Interv Radiol, No. 29:44, Jan. 1, 2018.
Schweitzer, et al., "Use of Heimlich Valve in compact Autotransfusion Device", The Journal of Trauma, vol. 27 No. 5, Jan. 1, 1987, 537-542.
European Search Report dated Feb. 27, 2020 for EP17851579.7.
European Search Report dated Apr. 23, 2021 for EP18872642.6.
European Search Report dated Jul. 9, 2021 for EP18876110.0.
European Search Report dated Sep. 7, 2017 for EP 09763115.4.
European Search Report dated Nov. 23, 2021 for EP19784978.9.
European Supplemental Search Report dated Aug. 17, 2012 for EP04811627.1.
Extended European Search Report dated Oct. 28, 2021 for EP19763606.1.
International Search Report and Written Opinion dated Jan. 25, 2007 for PCT/US2006/037766.
International Search Report and Written Opinion dated Apr. 2, 2019 for PCT/US2018/060089.
International Search Report and Written Opinion dated May 14, 2019 for PCT/US2018/058992.
International Search Report and Written Opinion dated Jun. 12, 2019 for PCT/US2019/020980.
International Search Report and Written Opinion dated Jul. 5, 2005 for PCT/US2004/38937.
International Search Report and Written Opinion dated Jul. 30, 2019 for PCT/US2019/026785.
International Search Report and Written Opinion dated Nov. 28, 2017 for PCT/US2017/041726.
International Search Report and Written Opinion dated Nov. 30, 2021 for PCT/US2021/045607.
International Search Report and Written Opinion dated Dec. 26, 2017 for PCT/US2017/051715.
International Search Report dated Nov. 18, 2009 for PCT/US2009/042868.
MedPlus, Inc., Tourniquet (Radial Artery Compression Device), http://www.bikudo.com/product_search/details/187473/tourniquet_radial_artey_compression_device.html Nov. 24, 2009.

(56) References Cited

OTHER PUBLICATIONS

Notice of Allowance dated Jan. 12, 2010 for U.S. Appl. No. 11/248,082.
Notice of Allowance dated Feb. 3, 2022 for U.S. Appl. No. 16/921,343.
Notice of Allowance dated Apr. 12, 2010 for U.S. Appl. No. 11/248,082.
Notice of Allowance dated Apr. 30, 2014 for U.S. Appl. No. 13/688,000.
Notice of Allowance dated Jun. 9, 2014 for U.S. Appl. No. 13/741,046.
Notice of Allowance dated Sep. 9, 2021 for U.S. Appl. No. 16/294,020.
Notice of Allowance dated Sep. 17, 2012 for U.S. Appl. No. 11/248,082.
Notice of Allowance dated Oct. 5, 2022 for U.S. Appl. No. 16/380,505.
Notice of Allowance dated Oct. 15, 2010 for U.S. Appl. No. 11/248,082.
Notice of Allowance dated Oct. 16, 2012 for U.S. Appl. No. 12/435,227.
Notice of Allowance dated Nov. 22, 2021 for U.S. Appl. No. 16/179,257.
Notice of Allowance dated Nov. 25, 2020 for U.S. Appl. No. 29/653,828.
Notice of Allowance dated Nov. 30, 2015 for U.S. Appl. No. 14/464,503.
Office Action dated Jan. 8, 2020 for U.S. Appl. No. 15/648,110.
Office Action dated Jan. 10, 2019 for U.S. Appl. No. 15/705,759.
Office Action dated Jan. 11, 2012 for U.S. Appl. No. 12/188,955.
Office Action dated Feb. 1, 2011 for U.S. Appl. No. 12/879,673.
Office Action dated Feb. 14, 2014 for U.S. Appl. No. 13/741,046.
Office Action dated Feb. 16, 2021 for U.S. Appl. No. 16/380,505.
Office Action dated Mar. 2, 2011 for U.S. Appl. No. 12/349,405.
Office Action dated Mar. 5, 2013 for U.S. Appl. No. 13/741,046.
Office Action dated Mar. 17, 2011 for U.S. Appl. No. 11/535,245.
Office Action dated Mar. 28, 2012 for U.S. Appl. No. 11/248,082.
Office Action dated Mar. 29, 2013 for U.S. Appl. No. 12/188,955.
Office Action dated Mar. 30, 2010 for U.S. Appl. No. 11/248,082.
Office Action dated Apr. 12, 2021 for U.S. Appl. No. 16/179,257.
Office Action dated Apr. 23, 2013 for U.S. Appl. No. 13/677,000.
Office Action dated May 2, 2014 for U.S. Appl. No. 12/188,955.
Office Action dated May 4, 2016 for U.S. Appl. No. 12/188,955.
Office Action dated May 10, 2021 for U.S. Appl. No. 16/294,020.
Office Action dated May 25, 2021 for U.S. Appl. No. 16/380,505.
Office Action dated May 26, 2011 for U.S. Appl. No. 12/188,955.
Office Action dated May 28, 2019 for U.S. Appl. No. 15/648,110.
Office Action dated Jun. 6, 2016 for U.S. Appl. No. 14/033,177.
Office Action dated Jun. 9, 2015 for U.S. Appl. No. 14/464,503.
Office Action dated Jun. 12, 2013 for U.S. Appl. No. 10/595,450.
Office Action dated Jun. 28, 2011 for U.S. Appl. No. 12/349,405.
Office Action dated Jun. 29, 2009 for U.S. Appl. No. 11/248,082.
Office Action dated Jul. 6, 2011 for U.S. Appl. No. 11/248,082.
Office Action dated Jul. 13, 2012 for U.S. Appl. No. 12/188,955.
Office Action dated Jul. 17, 2009 for U.S. Appl. No. 10/595,450.
Office Action dated Jul. 23, 2021 for U.S. Appl. No. 16/179,257.
International Search Report and Written Opinion dated Oct. 4, 2022 for PCT/US2022/072906, 13 pages.
Tremblay, et al., "Singel-Center Experience with 250 Tunnelled Pleural Catheter Insertions for Manignant Pleural Effusions", Chest, vol. 129 No. 2, Jan. 1, 2006, 362-368.
Vargas, et al., "Comparison of Silver Nitrate and Tetracycline as Pleural Sclerosing Agents in Rabbits", Chest, vol. 108 No. 4, Jan. 1, 1995, 1080-1083.
Vargas, et al., "Experimental Plerueodesis in Rabbits Induced by Silver Nitrate or Talc", ASAP, vol. 199 No. 5, May 1, 2001, 1516.
Notice of Allowance dated Jun. 10, 2013 for U.S. Appl. No. 13/469,849.
Office Action dated Aug. 2, 2013 for U.S. Appl. No. 13/688,000.
Zhou, et al., "Transient Ulnar Artery Compression Facilitates Transradial Access", Medicine, No. 95:48, Jan. 1, 2016.
European Examination Report dated Jun. 26, 2024 for EP18872642.6, 5 pages.
Office Action dated Apr. 5, 2022 for U.S. Appl. No. 16/380,505, 9 pages.
European Search Report dated Feb. 17, 2025 for EP22825995.8, 3 pages.
Pyles, et al., "Cannulation of the Dorsal Radial Artery: A New Technique", Anesthesia and Analgesia, vol. 61, No. 10, Oct. 1982, 3 pgs.
Office Action dated Feb. 10, 2025 for U.S. Appl. No. 17/657,067, 45 pages.

* cited by examiner

HEMOSTASIS DEVICES AND METHODS OF USE

RELATED APPLICATIONS

This application claims priority to U.S. Provisional Application No. 63/212,227, filed on Jun. 18, 2021 and titled, "Hemostasis Devices and Methods of Use," which is hereby incorporated by reference in its entirety.

TECHNICAL FIELD

The present disclosure relates generally to the field of medical devices used to provide compression or hemostasis at a vascular access puncture site. More particularly, some embodiments of the present disclosure relate to a hemostasis device used to provide hemostasis of the arteries of the lower leg and foot, including the anterior tibial artery, dorsalis pedis artery, posterior tibial artery, and peroneal artery, following vascular access.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

Interventional vascular procedures may be performed for both diagnostic and therapeutic reasons. Some vascular interventional procedures include percutaneous access of a vessel, such as an artery, with a needle followed by insertion of guidewires, dilators, sheaths, catheters, stents, balloons, etc. In some procedures, the vessel to be accessed may be a peripheral artery of the leg or foot. For example, the peripheral artery may be any one of the anterior tibial artery, the dorsalis pedis artery, the posterior tibial artery, and the peroneal artery. The vessel access creates a puncture site or hole in the vessel wall through which medical devices may be passed during a procedure. For example, the vessel access may facilitate procedures such as retrograde interventions for advanced peripheral arterial disease and critical limb ischemia of the lower leg. Additionally, the vessel access can allow genicular artery embolization for relief of long-term pain of the knee. At the conclusion of the procedure, the procedural devices may be removed and pressure or compression applied to the puncture site until hemostasis is achieved. The compression may be applied by a healthcare worker or by a hemostasis device, such as the hemostasis devices described herein. Such hemostasis devices may comprise bands for securement of the device to a foot of the patient and an inflatable compression member to apply a pressure or compressive force to the puncture site until hemostasis is achieved.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Figure 1:
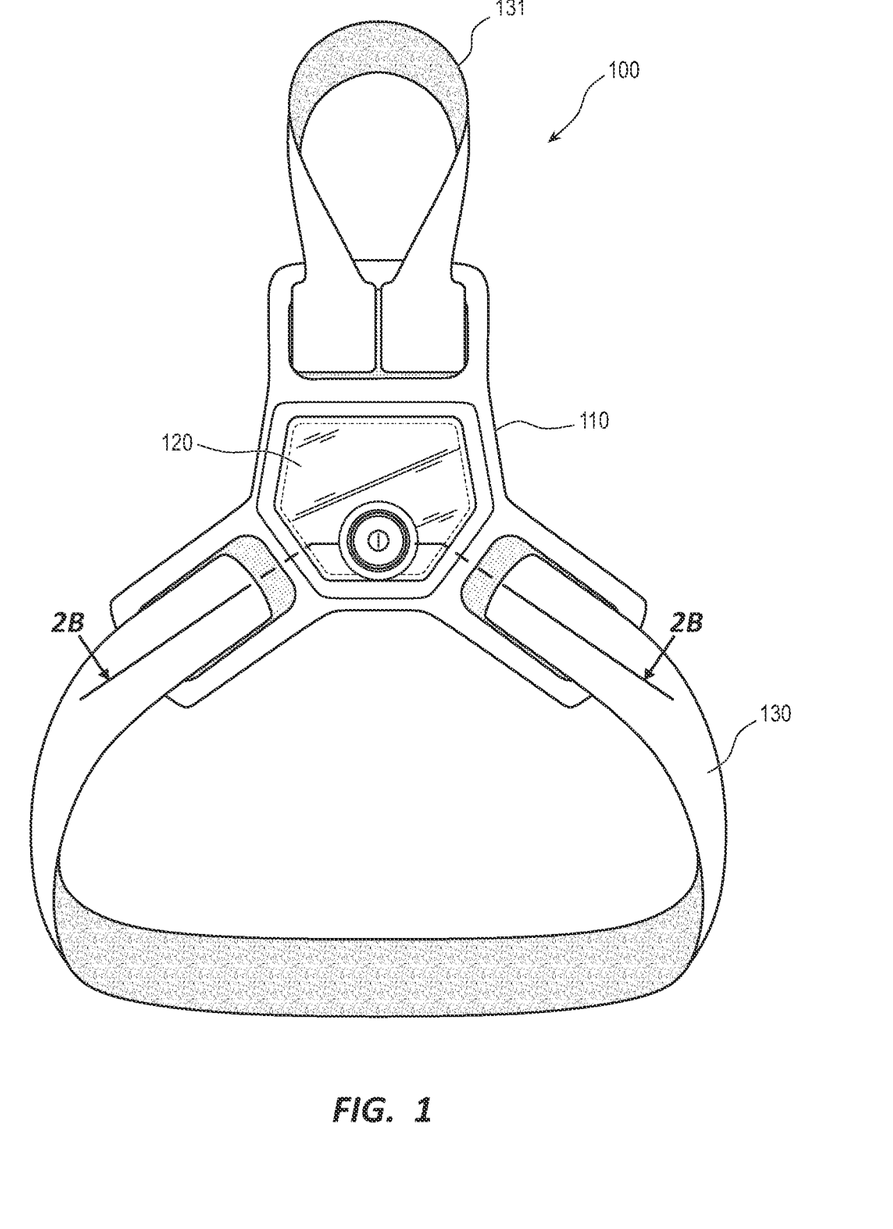
FIG. 1 is a top view of an embodiment of a hemostasis device.
Figures 2A, 2B:
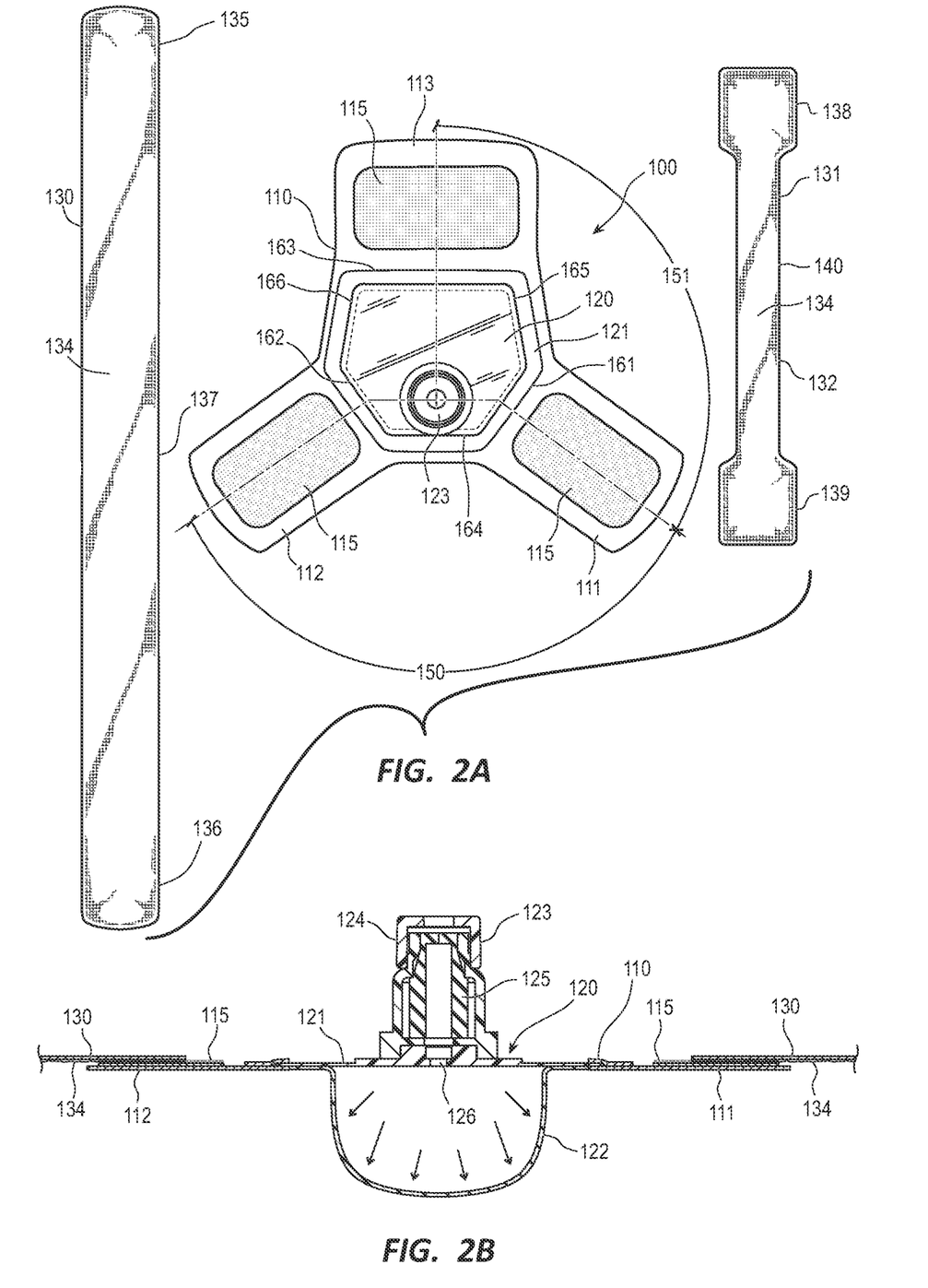
FIG. 2A is a top, exploded view of the hemostasis device of FIG. 1.
FIG. 2B is a cross-sectional view of the hemostasis device of FIG. 1 taken through section 2B-2B, with an inflatable bladder inflated.
Figure 3A:
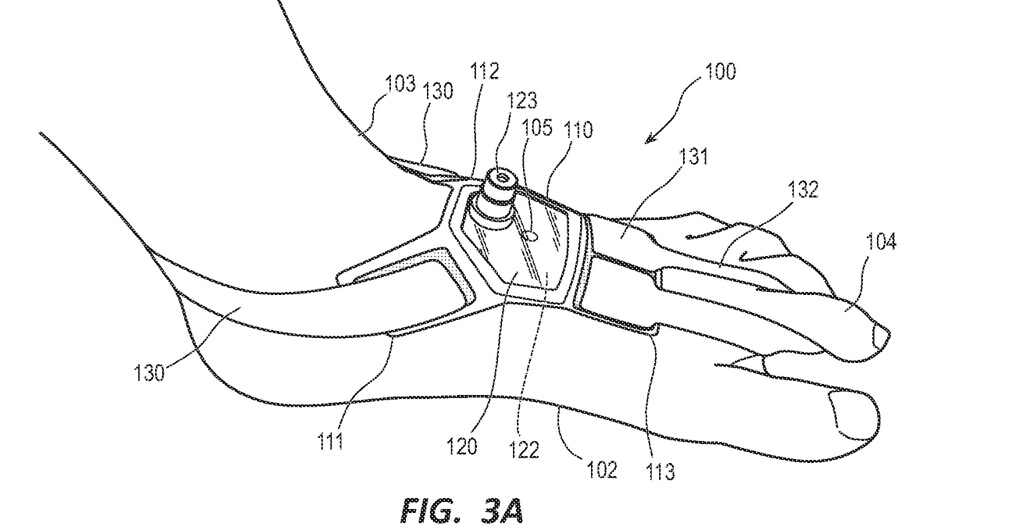
FIG. 3A is perspective view of the hemostasis device of FIG. 1 in a use configuration.
Figure 3B:
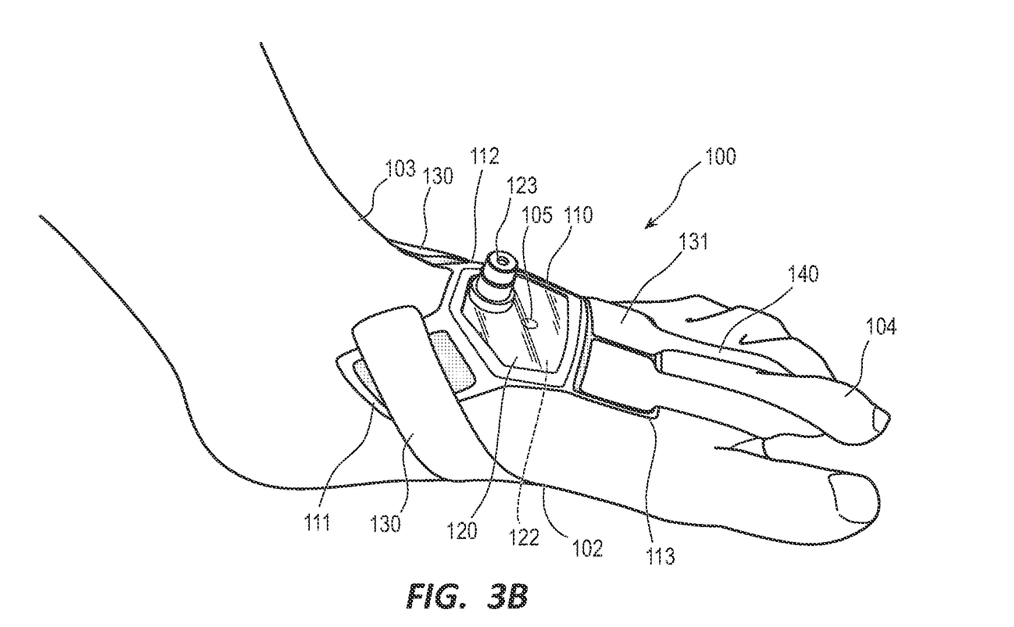
FIG. 3B is a perspective view of the hemostasis device of FIG. 1 in an alternative use configuration.

FIG. 1 provides a top view of a vascular access hemostasis device, system, or assembly 100. FIG. 2A provides a top, exploded view of the hemostasis device 100. FIG. 2B provides a cross-sectional view of the hemostasis device 100 with an inflatable bladder inflated. FIG. 3A provides a perspective view of the hemostasis device 100 in a use configuration. FIG. 3B provides a perspective view of the hemostasis device 100 in an alternative use configuration.

As illustrated in the embodiment of FIG. 1, the hemostasis device 100 includes a body 110, a compression member 120, an ankle band or strap 130, and a toe band or strap 131. The hemostasis device 100 may be configured to fit around a lower limb, such as a foot and a toe, to provide compression to a vascular access puncture site in the vasculature, including at any one of the anterior tibial artery, the dorsalis pedis artery, the posterior tibial artery, and the peroneal artery. Other vascular access sites are contemplated. The hemostasis device 100 may be configured to be a left lower limb device or a right lower limb device such that the hemostasis device 100 may provide a hemostasis puncture site in the left foot or right foot.

With reference to FIGS. 2A and 2B, the body 110 is shown to include a first coupling tab 111, a second coupling tab 112, and a third coupling tab 113. The body 110 may be formed from a flexible material that is conformable to a contour of an anatomical member, such as a foot. For example, the body, may be comprised of polyethylene, polypropylene, polyvinyl chloride, etc. Each of the coupling tabs 111, 112, 113 extend radially outward from a central portion of the body 110. Each of the coupling tabs 111, 112, 113 may include a releasable coupling member 115, such as a "hook" portion of a "hook-and-loop" material disposed on an upper surface. Other types of releasable securement members, such as pressure sensitive adhesives, buckles, magnets, snaps, clasps, etc. are contemplated to be within the scope of this disclosure.

The coupling tabs 111, 112, 113 are circumferentially disposed around a perimeter of the body 110. In the illustrated embodiment, the body 110 is in a substantially "Y" shape. Other shapes and configurations are contemplated within the scope of this disclosure. An angle 150 between the first coupling tab 111 and the second coupling tab 112 can range from about 60 degrees to about 120 degrees. An angle 151 between the first coupling tab 111 and the third coupling tab 113 can range from about 90 degrees to about 150 degrees.

The ankle band 130 and the toe band 131 may be formed from a flexible material, such as a plastic film, cloth, etc. The bands 130, 131 may comprise a releasable coupling member 134, such as a "loop" portion of a "hook-and-loop" material configured to releasably couple with the releasable coupling member 115. In some embodiments, the "loop" material may be integral to the material of the bands 130, 131. In other embodiments, the "loop" material may be coupled to a surface of the bands 130, 131. The "loop" material may cover a bottom surface of the bands 130, 131 over a full length of the bands 130, 131. In other embodiments, the "loop" material may cover a portion of the bottom surface of the bands 130, 131. Other types of releasable securement mechanisms, such as pressure sensitive adhesives, buckles, magnets, snaps, clasps, etc. are contemplated to be within the scope of this disclosure.

In the illustrated embodiment, the ankle band 130 comprises a first end portion 135, a second end portion 136, and an intermediate portion 137. In the depicted embodiment, the first end portion 135 is releasably couplable to the first coupling tab 111, the second end portion 136 is releasably couplable to the second coupling tab 112, and the intermediate portion 137 is configured to wrap around the patient's ankle such that a length of the ankle band 130 between the first and second coupling tabs 111, 112 is adjustable. Alternatively, the ankle band 130 may be wrapped around the patient's foot dependent upon the location of the puncture site. This configuration facilitates adjustment of the length of the ankle band 130 to fit a range of ankle circumferences. In the illustrated embodiment the ankle band 130 is fully detachable from the body 110. In other embodiments, the ankle band 130 may be fixedly attached to the body 110 at the first end portion 135 and releasably coupled to the body 110 at the second end portion 136 or vice versa. Additionally, embodiments wherein the ankle band 130 is fixedly attached to the body 110 at both ends, including embodiments wherein the ankle band 130 comprises an elastic material, are likewise within the scope of this disclosure.

In the illustrated embodiment, the toe band 131 comprises a first end portion 138, a second end portion 139, and an intermediate portion 140. In the depicted embodiment, the first end portion 138 is releasably couplable to the third coupling tab 113, the second end portion 139 is releasably couplable to the third coupling tab 113, and the intermediate portion 140 is configured to wrap around the patient's toe such that a length of the toe band 131 between the third coupling tab 113 is adjustable. This configuration facilitates adjustment of the length of the toe band 131 to fit a range of distances of the puncture site from the patient's toe. In another configuration, the toe band 131 may extend between adjacent toes of the patient with the first end portion 138 releasably coupled to the third coupling tab 113 and the second end portion 139 releasably coupled to the ankle band 130 at a bottom surface of the patient's foot. In the illustrated embodiment the toe band 131 is fully detachable from the body 110. In another embodiment, the toe band 131 may be fixedly attached to the body 110 at the first end portion 138 and releasably coupled to the body 110 at the second end portion 139 or vice versa. Additionally, embodiments wherein the toe band 131 is fixedly attached to the body 110 at both ends, including embodiments wherein the toe band 131 comprises an elastic material, are likewise within the scope of this disclosure. A width of the intermediate portion 140 may be less than a width of the first and second end portions 138, 139. This configuration may facilitate greater patient comfort as the toe band 131 wraps around or extends between the patient's toes. The toe band 131 may be configured to wrap around or extend between any of the patient's toes.

Additionally, in embodiments wherein one or more ends of the ankle band 130 and/or toe band 131 are releasably coupleable to the coupling tabs 111, 112, 113 (such as by a hook and loop fastener) the angle at which the ankle band 130 and/or toe band 131 couples to the respective coupling tab 111, 112, 113 may be adjustable over a range. During a procedure, a practitioner can couple one or more ends of the ankle band 130 and/or toe band 131 to a coupling tab 111, 112, 113 at an angle positions the body 110 at a desired position as well as the bands at desired positions on the patient's anatomy. Use of releasably coupleable bands 130, 131 may thus facilitate adjustability and conformability of the device to a patient's anatomy and the position of an access site.

With continued reference to FIG. 2A, the compression member 120 may be configured to be positioned over the vascular access puncture site on the foot of a patient. The compression member 120 may be configured to be inflatable as illustrated in the embodiment of FIG. 2B. In some embodiments, the compression member 120 may be configured to provide compression using a mechanical system including rigid compression pads, resilient or elastomeric compression pads, and/or mechanisms configured to displace the pads such as a threaded post. In other embodiments, the compression member 120 may comprise at least one gauze pad. In still other embodiments, the compression member 120 may be configured to compress the vascular access puncture site using any suitable mechanism.

As illustrated in FIGS. 2A and 2B, the compression member 120 comprises a top plate 121, an inflatable bladder 122, and an inflatable port 123. The top plate 121 may be formed of clear or translucent material to allow observation of the puncture site. For example, the top plate 121 may comprise polycarbonate, polystyrene, styrene copolymers, polyethylene teraphthalate, acrylic, polyethylene, polypropylene, etc. The top plate 121 may be sealingly coupled to the body 110. As depicted, the top plate includes a first side 161, a second side 162, a third side 163, a fourth side 164, a fifth side 165, and a sixth side 166. The first side 161 is adjacent the first coupling tab 111, the second side 162 is adjacent the second coupling tab 112, and the third side 163 is adjacent the third coupling tab 113. Other shapes of the top plate 121 are contemplated. The top plate 121 may be formed in a concave shape relative to a top surface such that the top plate 121 conforms to an anatomical shape of the foot.

The inflatable bladder 122 comprises a flexible wall configured to extend downward from the top plate 121, as depicted in FIG. 2B, when the bladder 122 is filled with air or fluid such that a compressive force may be applied to the vascular access puncture site. The bladder 122 may be sealed at its edges to the bottom surface of the top plate 121. The bladder 122 may be transparent or translucent such that the puncture site can be seen through the flexible wall. The bladder 122 may be formed from any suitable, flexible, transparent or translucent material, such as polyethylene, polypropylene, etc. The fluid may comprise sterile water, normal saline solution, or any other suitable medical fluid. In some embodiments, a target may be printed on an exterior or interior service of the wall of the bladder 122. The target may facilitate alignment of the compression member 120 with the vascular access puncture site.

In the illustrated embodiment, the inflation port 123 is coupled to the top surface of the top plate 121 such that the inflation port 123 is in fluid communication with the inflatable bladder 245 through an orifice 126 through the top plate 121. The inflation port 123 is positioned on the top plate 121 toward an outer perimeter of the top plate 121 adjacent the fourth side 164 and between the first side 161 and second side 162 such that the inflation port 123 does not obstruct visualization of the vascular access puncture site.

The inflation port 123 may comprise a valve member 125 and a housing 124 configured to retain the valve member 125. The housing 124 can include a female Luer fitting to facilitate releasably coupling of a medical device, such as a syringe, to the inflation port 123. When coupled to the syringe, the valve member 125 may be axially displaced such that the inflation port 123 is open and air or liquid may be injected into the inflatable bladder 122 to inflate the compression member 120 to provide a compressive force at the vascular access puncture site. Additionally, air or liquid may be removed from the inflatable bladder 122 to deflate the compression member 120 and reduce the compressive force on the vascular access puncture site. In certain embodiments the valve member 125 may comprise a pre-slit septum such that a non-Luer access device coupled to the syringe can penetrate the septum to access the inflation port 123. Additionally, the inflation port 123 may be configured to mate only with a specified inflation device, including embodiments wherein the inflation device is not configured to mate with a standard luer connector, in order to reduce the chance of accidental coupling of the inflation device to other medical devices accessing the patient's body.

In use, in some embodiments, a retrograde procedure may be performed by a healthcare worker on the patient where access to a peripheral artery of the leg, such as the anterior tibial artery, the dorsalis pedis artery, the posterior tibial artery, and the peroneal artery, is necessary due to blockage of arteries of the upper leg. The retrograde procedure may include interventions for advanced peripheral arterial disease and critical limb ischemia of the lower leg. Additionally, the vessel access can allow genicular artery embolization for relief of long-term pain of the knee.

At the conclusion of the retrograde procedure, compressive pressure or force may be applied to the vascular access puncture site of the distal radial artery to facilitate hemostasis of the vascular access puncture site as quickly as possible and without loss of a significant blood volume and with reduced time required from the healthcare worker. Referring to FIGS. 3A and 3B, the hemostasis device 100 may be utilized to apply the compressive pressure to a vascular access puncture site 105. The compression member 120 may be positioned over the vascular access puncture site 105 at a dorsal or medial aspect of a patient's foot 102. As shown in FIG. 3A, the ankle band 130 may be extended around the patient's ankle 103 and be releasably coupled to the first and second coupling tabs 111, 112 to restrict distal movement of the hemostasis device relative to the patient's foot 102. Alternatively, as shown in FIG. 3B, the ankle band 130 may extend around the patient's foot 102 to provide a downward force to the hemostasis device. The toe band 131 may extend toward the patient's toes 104 such that the intermediate portion 140 is wrapped around any one of the patient's toes 104 and may be releasably coupled to the third coupling tab 113 to restrict proximal movement of the hemostasis device 100 relative to the patient's foot 102.

Following placement of the hemostasis device 100, the syringe (not shown) may be coupled to the inflation port 123 and air or liquid injected through inflation port 123 into the inflatable bladder 122 such that the inflatable bladder 122 is inflated and applies a compressive pressure or force to the vascular access puncture site 105. In some embodiments, the syringe may be coupled to the inflation port 123 to remove a portion of the air or liquid within the inflatable bladder 122 such that the inflatable bladder 122 is partially deflated. In other embodiments, the syringe may be coupled to the inflation port 123 to remove all of the air or liquid within the inflation bladder 122 such that the inflatable bladder 122 is fully deflated and the compressive force is relieved from the vascular access puncture site 105.

FIGS. 4-7B depict an embodiment of a hemostasis device 200 that resembles the hemostasis device 100 described above in certain respects. Accordingly, like features are designated with like reference numerals, with the leading digits incremented to "2." For example, the embodiment depicted in FIGS. 4-7B includes a compression member 220 that may, in some respects, resemble the compression member 120 of FIG. 1. Relevant disclosure set forth above regarding similarly identified features thus may not be repeated hereafter. Moreover, specific features of the hemostasis device 100 and related components shown in FIGS. 1-3B may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the hemostasis device 200 and related components depicted in FIGS. 4-7B. Any suitable combination of the features, and variations of the same, described with respect to the hemostasis device 100 and related components illustrated in FIGS. 1-3B can be employed with the hemostasis device 200 and related components of FIGS. 4-7B, and vice versa. This pattern of disclosure applies equally to further embodiments depicted in subsequent figures and described hereafter, wherein the leading digits may be further incremented.

Figure 4:
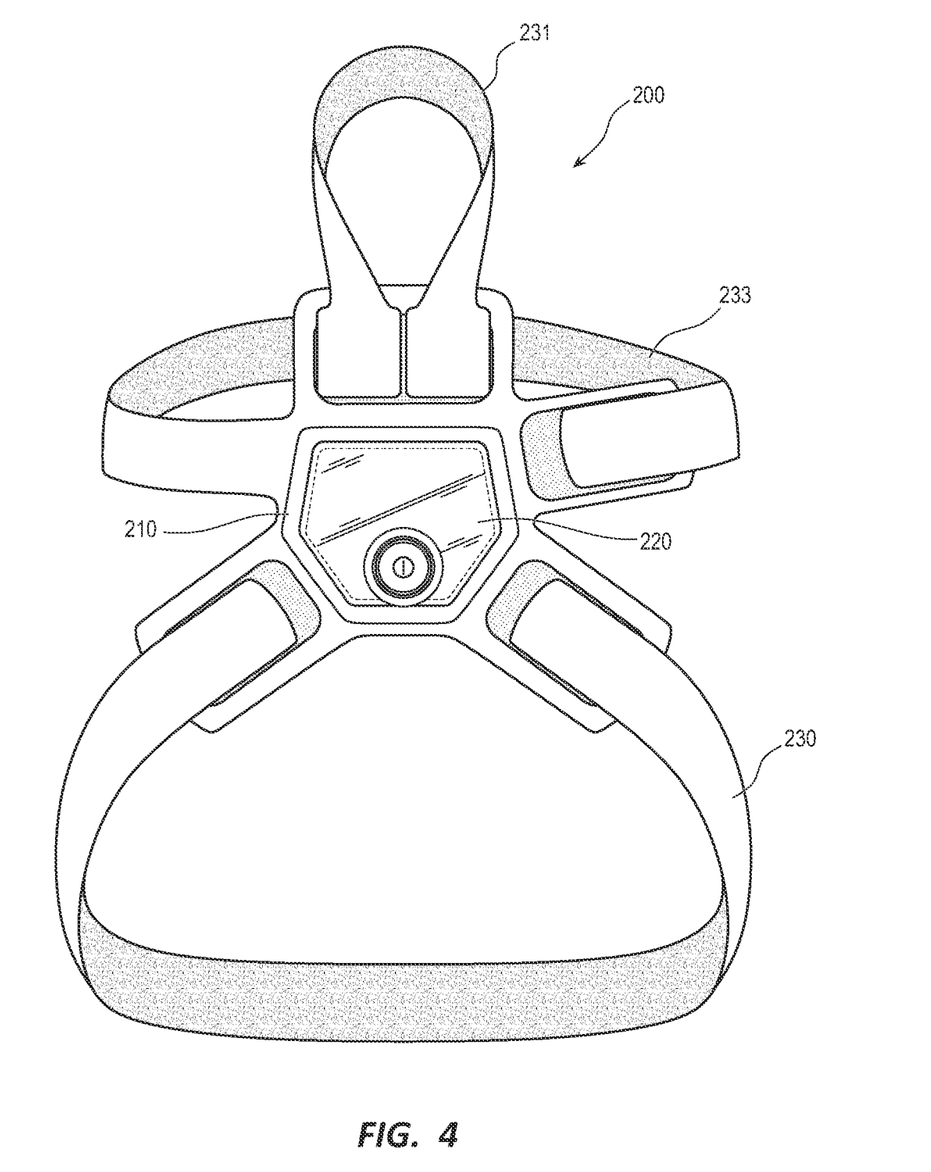
FIG. 4 is a top view of another embodiment of a hemostasis device.
Figure 5:
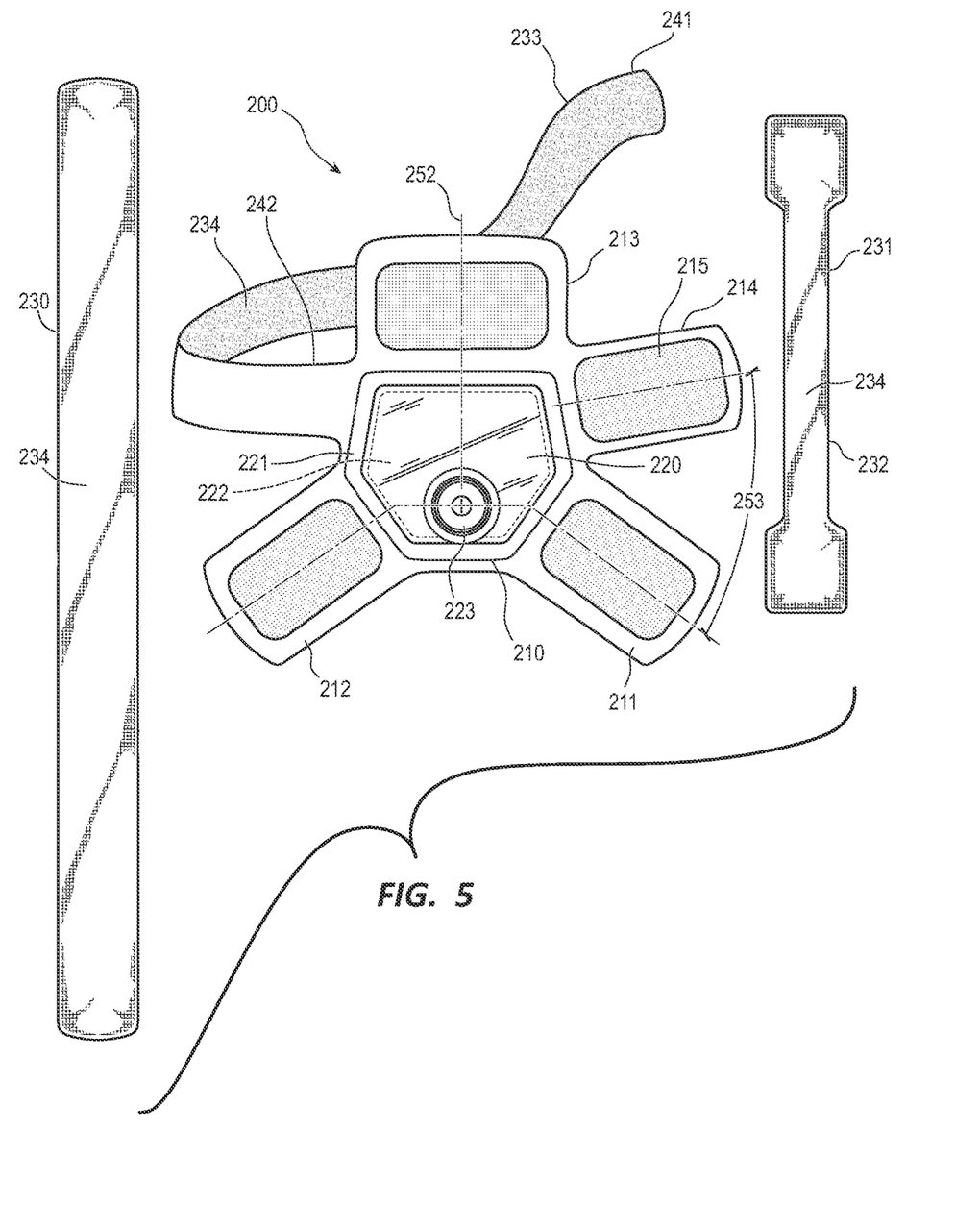
FIG. 5 is a top, exploded view of the hemostasis device of FIG. 4.
Figure 6:
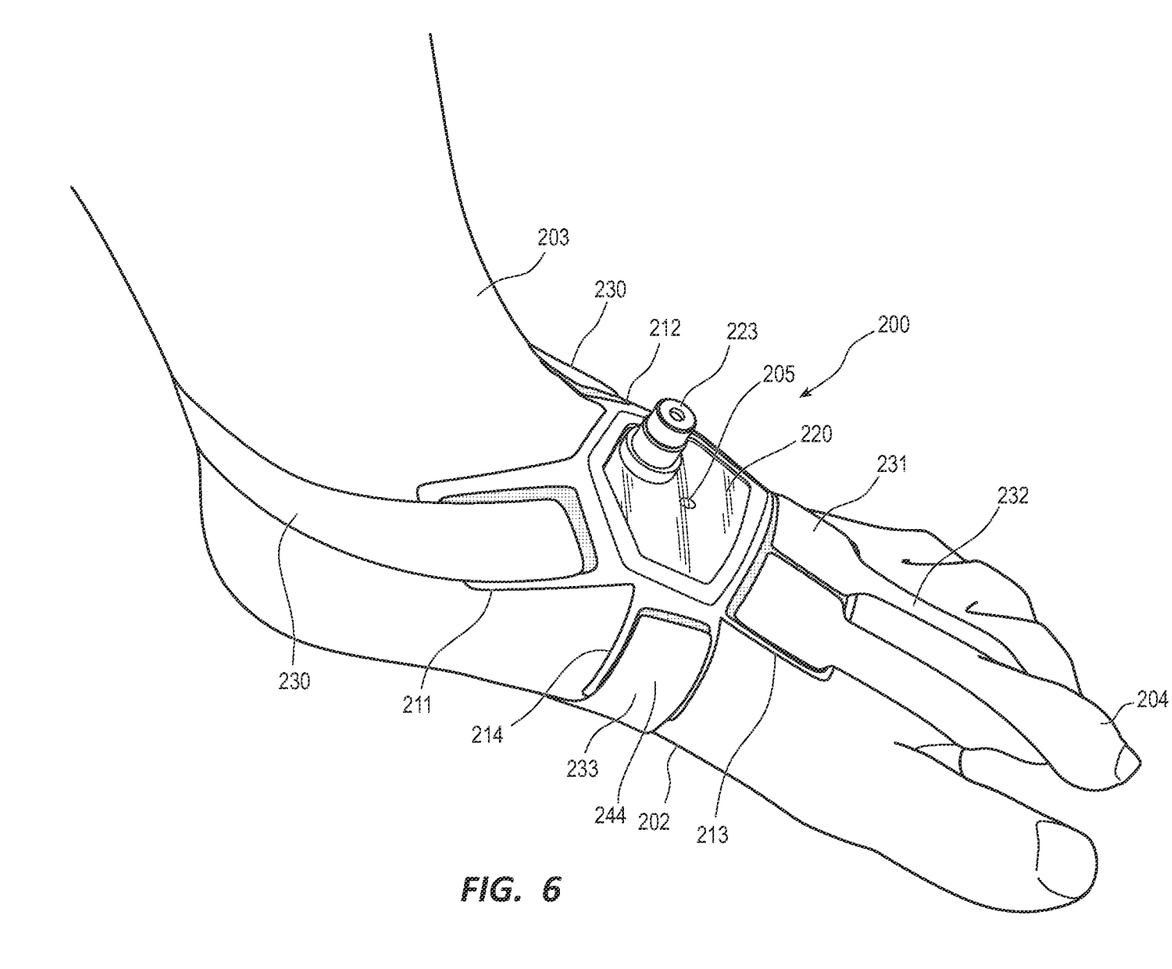
FIG. 6 is a perspective view of the hemostasis device of FIG. 4 in a use configuration.
Figure 7A:
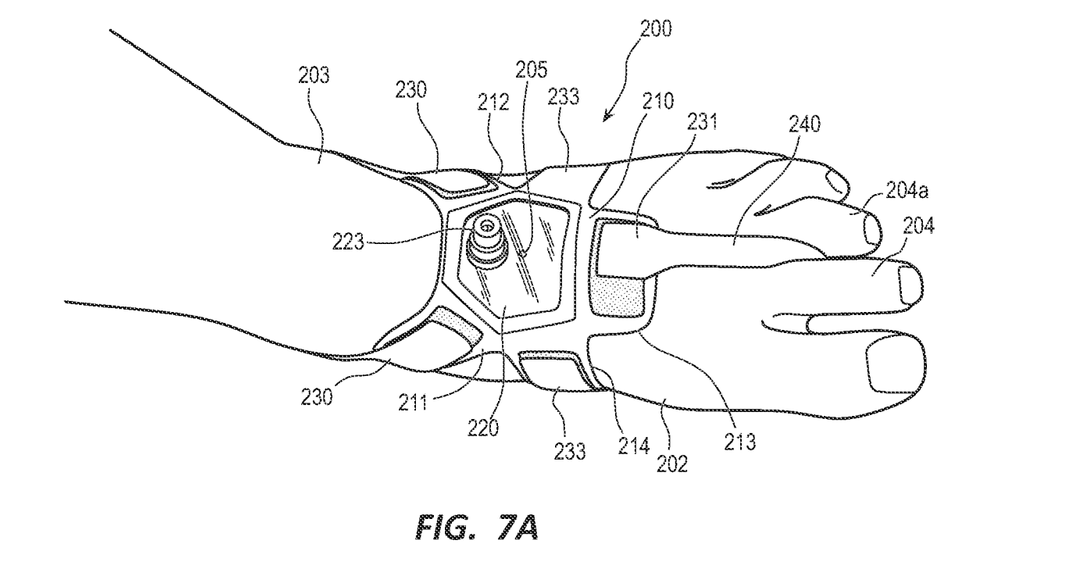
FIG. 7A is a top perspective view of the hemostasis device of FIG. 4 in an alternative use configuration.
Figure 7B:
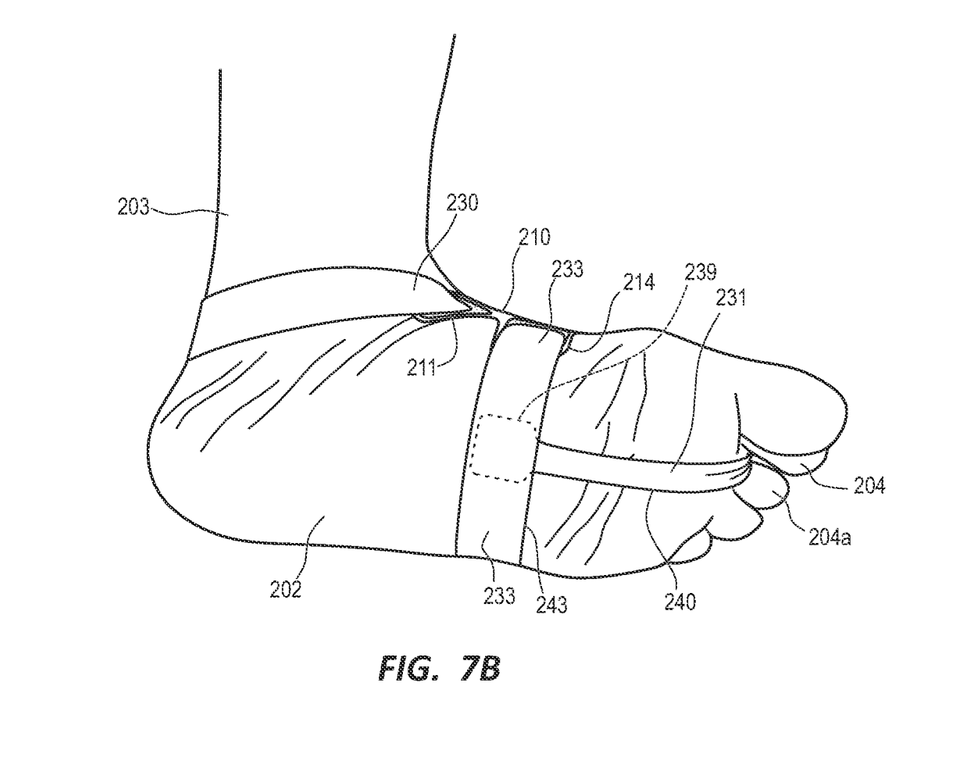
FIG. 7B is a bottom perspective view of the hemostasis device of FIG. 4 in the alternative use configuration.

FIG. 4 provides a top view of a vascular access hemostasis device, system, or assembly 200. FIG. 5 provides a top, exploded view of the hemostasis device 200. FIG. 6 provides a perspective view of the hemostasis device 200 in a use configuration. FIGS. 7A and 7B provide a perspective view of the hemostasis device 200 in an alternative use configuration. As illustrated in the embodiment of FIG. 4, the hemostasis device 200 includes a body 210, a compression member 220, an ankle band or strap 230, a toe band or strap 231, and a foot band or strap 233 configured to wrap around a patient's foot. The hemostasis device 200 may include a first coupling tab 211, a second coupling tab 212, and a third coupling tab 213, which may be disposed a the same or different relative positions and angles as the coupling tabs 111, 112, 113 of the embodiment of FIGS. 1-3B.

As illustrated in FIG. 5, the body 210 includes a fourth coupling tab 214 extending radially outward and disposed between the first coupling tab 211 and the third coupling tab 213. An angle 253 between the first coupling tab 211 and the fourth coupling tab 214 can range from about 30 degrees to about 90 degrees. The fourth coupling tab 214 includes a releasable coupling member 215, such as a "hook" portion of a "hook-and-loop" material. The foot band 233 includes a releasable coupling member 234, such as a "loop" portion of the "hook-and-loop" material. A first end portion 241 is releasably couplable to the fourth coupling tab 214. In the illustrated embodiment, a second end portion 242 is fixedly coupled to the body 210 between the second coupling tab 212 and the third coupling tab 313. In certain embodiments, the foot band 233 and the body 210 may include a unibody construction. In other embodiments, the body 210 may include a fifth coupling tab, and the second end portion 242 may be releasably couplable to the fifth coupling tab.

As with the embodiment of FIGS. 1-3B, hemostasis device 200 of FIG. 5 may be configured such that any of the bands 230, 231, 233 is fixedly coupled to the body 210 at one or both ends and/or embodiments wherein any of the bands 230, 231, 233 are releasably coupleable to the body 210 at one or both ends. As also discussed in connection with the embodiment of FIGS. 1-3B, in embodiments wherein an end of any of the bands 230, 231, 233 is releasably coupleable to any of the coupling tabs 211, 212, 213, 214 (or any other portion of the body) the angle at which the band 230, 231, 233 couples to the body may be adjustable by a practitioner during use.

In use, as shown in FIG. 6, the compression member 220 of the hemostasis device 200 may be positioned over the vascular access puncture site 205 at a dorsal or medial aspect of a patient's foot 202. The ankle band 230 may be extended around the patient's ankle 203 and be releasably coupled to the first and second coupling tabs 211, 212 to restrict distal movement of the hemostasis device 200. The toe band 231 may extend toward and be wrapped around any one of the patient's toes 204 and be releasably coupled to the third coupling tab 213 to restrict proximal movement of the hemostasis device 100. Alternatively, as shown in FIGS. 7A and 7B, the toe band 231 may extend toward the patient's toes 204 and pass between adjacent toes 204, 204a (embodiments wherein the toe band 231 is configured to pass between any of the patients toes are within the scope of this disclosure as well). The second end portion 239 may be releasably coupled to an intermediate portion 243 of the foot band 233 at a bottom surface of the patient's foot 202. The foot band 233 is wrapped around the patient's foot 202 and the first end 241 is releasably coupled to the fourth coupling tab 214 to provide a downward force to the hemostasis device 200.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified. For example, a method of applying a compressive force to a vascular access puncture site may include one or more of the following steps: positioning a compression member of a hemostasis device over a vascular access puncture site; wrapping a first securement band around an ankle or foot of a patient; releasably coupling a first end of the first securement band to a first coupling tab of the hemostasis device; releasably coupling a second end of the first securement band to a second coupling tab of the hemostasis device; extending a second securement band around a toe or between adjacent toes of the patient; releasably coupling a first end of the second securement band to a third coupling tab of the hemostasis device; releasably coupling a second end of the second securement band to the third coupling tab of the hemostasis device; and inflating the compression member to apply a compressive force to the vascular access puncture site. Other steps are also contemplated.

In the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment.

The phrases "coupled to" and "in communication with" refer to any form of interaction between two or more entities, including mechanical, electrical, magnetic, electromagnetic, fluid, and thermal interaction. Two components may be coupled to or in communication with each other even though they are not in direct contact with each other. For example, two components may be coupled to or in communication with each other through an intermediate component.

"Fluid" is used in its broadest sense, to refer to any fluid, including both liquids and gases as well as solutions, compounds, suspensions, etc., which generally behave as fluids.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially perpendicular" is recited with respect to a feature, it is understood that in further embodiments, the feature can have a precisely perpendicular configuration.

The terms "a" and "an" can be described as one, but not limited to one. For example, although the disclosure may recite a housing having "a stopper," the disclosure also contemplates that the housing can have two or more stoppers.

Unless otherwise stated, all ranges include both endpoints and all numbers between the endpoints.

Recitation in the claims of the term "first" with respect to a feature or element does not necessarily imply the existence of a second or additional such feature or element.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A hemostasis device, comprising:
 a body comprising:
  a first coupling tab;
  a second coupling tab;
  a third coupling tab; and
 a compression member configured to compress a vascular puncture site;
 a plurality of securement bands, comprising:
  a first securement band releasably coupled to the first and second coupling tabs and configured to wrap around a patient's ankle or foot; and
  a second securement band comprising:
   a first end portion releasably coupled to the third coupling tab; and
   a second end portion releasably coupled to the third coupling tab;
  wherein the second securement band is configured to wrap around the patient's toe or extend between adjacent toes of the patient.

2. The hemostasis device of claim 1, wherein the body comprises a "Y" shape.

3. The hemostasis device of claim 1,
 wherein an angle between the first coupling tab and the second coupling tab ranges from 60 degrees to 120 degrees; and
 wherein an angle between the first or second coupling tab and the third coupling tab ranges from 90 degrees to 150 degrees.

4. The hemostasis device of claim 1, wherein each of the first, second, and third coupling tabs comprises a hook portion of a hook-and-loop material.

5. The hemostasis device of claim 1, wherein each of the first and second securement bands comprises a loop portion of a hook-and-loop material.

6. The hemostasis device of claim 1, wherein the second securement band comprises a narrowed middle portion disposed between wide end portions.

7. The hemostasis device of claim 1, wherein the body further comprises a fourth coupling tab circumferentially disposed between the first and third coupling tabs.

8. The hemostasis device of claim 7, wherein an angle between the first coupling tab and the fourth coupling tab ranges from 30 degrees to 90 degrees.

9. The hemostasis device of claim 8, wherein the fourth coupling tab comprises a hook portion of a hook-and-loop material.

10. The hemostasis device of claim 8, further comprising a third securement band releasably coupled to the fourth coupling tab and fixedly coupled to the body circumferentially between the second coupling tab and the third coupling tab, wherein the third securement band is configured to wrap around the patient's foot.

11. The hemostasis device of claim 10, wherein the third securement band comprises a loop portion of a first hook-and-loop material.

12. The hemostasis device of claim 11, wherein the second securement band comprises a hook portion of a hook-and-loop material.

13. The hemostasis device of claim 1, further comprising:
 a fourth coupling tab circumferentially disposed between the first coupling tab and the third coupling tab; and
 a third securement band releasably coupled to the fourth coupling tab and fixedly coupled to the body circumferentially between the second coupling tab and the third coupling tab.

14. The hemostasis device of claim 13,
 wherein an angle between the first coupling tab and the second coupling tab ranges from 60 degrees to 120 degrees;
 wherein an angle between the first coupling tab and the third coupling tab ranges from 90 degrees to 150 degrees; and
 wherein an angle between the first coupling tab and the fourth coupling tab ranges from 30 degrees to 90 degrees.

15. The hemostasis device of claim 14, wherein the compression member comprises:
 a top plate;
 an inflatable bladder coupled to a bottom surface of the top plate; and an inflation port in fluid communication with the inflatable bladder.

16. The hemostasis device of claim 15, wherein the inflation port comprises a self-closing valve member coupled to the top plate.

17. A method of applying a compressive force to a vascular access puncture site, comprising:
 positioning a compression member of a hemostasis device over a vascular access puncture site;
 wrapping a first securement band around an ankle or foot of a patient; releasably coupling a first end of the first securement band to a first coupling tab of the hemostasis device;
 releasably coupling a second end of the first securement band to a second coupling tab of the hemostasis device;
 extending a second securement band around a toe or between adjacent toes of the patient;
 releasably coupling a first end of the second securement band to a third coupling tab of the hemostasis device;
 releasably coupling a second end of the second securement band to the third coupling tab of the hemostasis device; and
 inflating the compression member to apply a compressive force to the vascular access puncture site.

18. The method of claim 17, further comprising:
 wrapping a third securement band around the foot of the patient; and
 releasably coupling a first end of the third securement band to a fourth tab of the hemostasis device.

* * * * *

UNITED STATES PATENT AND TRADEMARK OFFICE
CERTIFICATE OF CORRECTION

| | | |
|---|---|---|
| PATENT NO. | : 12,426,864 B2 | Page 1 of 1 |
| APPLICATION NO. | : 17/806653 | |
| DATED | : September 30, 2025 | |
| INVENTOR(S) | : Stephenson et al. | |

It is certified that error appears in the above-identified patent and that said Letters Patent is hereby corrected as shown below:

In the Claims

Column 10, Line 5, Claim 12 reads, ". . . of a hook-and-look material..." which should read, ". . . of a second hook-and-loop material..."

Signed and Sealed this
Sixth Day of January, 2026

John A. Squires
*Director of the United States Patent and Trademark Office*